United States Patent
Dias et al.

(10) Patent No.: US 6,309,426 B1
(45) Date of Patent: Oct. 30, 2001

(54) HAIR COLORING COMPOSITIONS

(75) Inventors: Louis Carlos Dias; James Charles Dunbar, both of Weybridge; Dominic Pratt, Kingson Upon Thames, all of (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/331,682

(22) PCT Filed: Dec. 9, 1997

(86) PCT No.: PCT/US97/22452

§ 371 Date: Jun. 23, 1999

§ 102(e) Date: Jun. 23, 1999

(87) PCT Pub. No.: WO98/27941

PCT Pub. Date: Jul. 2, 1998

(30) Foreign Application Priority Data

Dec. 23, 1996 (GB) .................................. 9626711

(51) Int. Cl.$^7$ ..................................... A61K 7/13
(52) U.S. Cl. ...................... 8/407; 8/406; 8/408
(58) Field of Search ................. 8/406, 407, 408

(56) References Cited

U.S. PATENT DOCUMENTS

| | | | |
|---|---|---|---|
| 4,885,006 | 12/1989 | Grollier et al. ....................... | 8/423 |
| 5,100,436 | 3/1992 | Wenke ...................... | 8/405 |
| 5,180,397 | * 1/1993 | Grollier et al. . | |
| 5,207,798 | 5/1993 | Cotteret et al. ........................ | 8/408 |
| 5,279,619 | 1/1994 | Cotteret et al. ........................ | 8/406 |
| 5,316,551 | 5/1994 | Wenke ...................... | 8/406 |
| 5,368,610 | 11/1994 | Chan et al. ............... | 8/406 |
| 5,391,206 | 2/1995 | Cotteret ................... | 8/408 |
| 5,500,022 | 3/1996 | Cotteret ................... | 8/410 |
| 5,683,474 | * 11/1997 | Cotteret et al. ........................ | 8/408 |
| 6,024,769 | * 2/2000 | Cotteret ................... | 8/408 |

* cited by examiner

Primary Examiner—Margaret Einsmann
(74) Attorney, Agent, or Firm—Brent M. Peebles; Stephen T. Murphy

(57) ABSTRACT

A hair coloring composition present in a single package suitable for direct application to the hair wherein the hair coloring mixture comprises: a) an oxidising agent; and b) an oxidative hair coloring agent; and wherein the combined mixture of a) and b) has a pH in the range of from about 1 to about 5 and wherein the resultant color delivered to the hair (Delta E), after at least about 1 month of storage at room temperature, is up to about 75%, preferably up to about 85%, more preferably up to about 90% and most preferably up to about 95% of the total color delivered to the hair (Delta E) from a mixture of a) and b) on application. The products are storage stable, re-usable and can provide both excellent hair coloring and in-use efficacy benefits as well as improved color development potential after storage at room temperature.

21 Claims, No Drawings

HAIR COLORING COMPOSITIONS

TECHNICAL FIELD

This invention relates to hair coloring compositions and processes for coloring hair, and more especially to hair coloring compositions comprising either, (i) a separate, storage stable, oxidising agent component in combination with a separate, storage stable, oxidative hair coloring component, each at an acidic pH of between about 1 and about 6, which, when combined, result in a combined, storage stable, re-usable, coloring composition having a pH of between about 1 and about 5, or, (ii) a storage stable, re-usable mixture of oxidising agent and oxidative hair coloring agent at a combined acidic pH of between about 1 and about 5.

BACKGROUND OF THE INVENTION

The desire to alter the color of human hair is not a facet of modern times. Since the days of the Roman Empire the color of human hair has been routinely altered to accommodate the changes of fashion and style. However the attainment of precise initial colors which are retained by the hair for a desirable period has remained a more elusive goal. The difficulties in the development of hair coloring compositions which can deliver precise long-lasting colors are in part due to the inherent structure of the hair itself and in part due to the necessary conditions of effective hair coloration processes.

Over the years significant effort has been directed towards the elimination of many of the problems associated with the dyeing of human hair. Various approaches to hair dyeing have been developed, these include, direct action dyes, natural dyes, metallic dyes and oxidative dyes.

To color human or animal hair using oxidative dye technology the hair is generally treated with a mixture of oxidative hair coloring agents and an oxidising agent.

Oxidative hair coloring agents and oxidising agents can be used to deliver a variety of hair colors to the hair. However substantial improvement is needed in the area of application characteristics of coloring compositions, such as, time to prepare the coloring composition, mess on application, waste of product not used, waste of packaging (from use of multiple component systems), storage stability (of the coloring composition once mixed), and the ability to re-use the mixed coloring composition. Re-use, of a coloring composition, as defined herein, means, correction of mistakes, touching up or root coverage, and future re-coloring of the hair with the same product as well as color and/or strand tests on small areas of hair.

In addition to the improvements in application charateristics as detailed hereinbefore, substantial improvement is needed in the area of coloring characteristics such as, color saturation, color development, precise initial color consistency, improved wash fastness, improved hair condition and levels of hair damage.

Conventional oxidative hair dyeing compositions generally comprise at least two separately packaged components. Typically, these components include oxidising agent (at low pH), such as hydrogen peroxide, and dyeing material (at high pH), such as oxidative hair coloring agents. In order to facilitate the hair dyeing process these separately packaged components are generally admixed just prior to application of the coloring composition to the hair. After mixing, such, high pH, compositions tend to degrade which can lead to reduced or impaired coloring ability. High pH hair coloring compositions are typically used soon after admixing. In general, any excess, admixed, coloring composition is disposed of after application of the required amount to the hair. Furthermore, such conventional coloring compositions, once mixed, cannot be stored and/or re-used, as the activated oxidative dyeing system rapidly deteriorates over time. Thus, it would be desirable to develop an oxidative hair coloring composition which comprises both oxidising agent and oxidative coloring agents which is storage stable and/or re-useable.

As detailed hereinbefore conventional oxidative hair dyeing compositions generally comprise at least two separately packaged components. In addition to the time required to effectively mix these components, the mixing process itself can be both messy and wasteful as well as causing added inconvenience to the user. Thus, it would be desirable to develop a convenient and easy-to-use method for the delivery of oxidative hair coloring compositions to the hair which does not require mixing of the oxidising and coloring components.

It would also be desirable to develop a hair coloring composition comprising an oxidising agent and an oxidative hair coloring agent which can be stored as separately packaged, stable, low pH, components which, on mixing, provides a shelf-stable, low pH mixture which is suitable for direct application to the hair. This low pH mixture could be stored and re-used. This would allow the consumer to correct mistakes, touch up roots or re-apply product,without re-purchase.

It has been found that, at low pH, mixtures of oxidising agents and oxidative hair coloring agents, can be packaged together, in a single pack, and are storage stable and re-usable. It has also been found that such low pH mixtures of oxidising agent and oxidative hair coloring agents provide improved initial hair coloring attributes versus conventional, high pH, compositions. It has also been found that, low pH mixtures of oxidising agent and oxidative hair coloring agents, which have been stored at room temperature, provide improved color development potential versus conventional coloring compositions.

It has also been found that, at low pH, both the oxidising agent and oxidative hair coloring agents are stable over time, and can be stored as such.

It is an object of the present invention to provide, low pH hair coloring compositions comprising both oxidising agents and oxidative hair coloring agent which are singly packaged, which are fast acting, simple to use, storage stable, and which are re-usable.

It has been found that the above objects can be met by the low pH, storage stable, re-usable hair coloring compositions according to the present invention.

All percentages are by weight of the final compositions in the form intended to be used unless specified otherwise.

SUMMARY OF THE INVENTION

The subject of the present invention is a hair coloring composition suitable for the treatment of human or animal hair.

According to one aspect of the present invention there is provided a hair coloring composition wherein the coloring mixture is present in a single package suitable for direct application to the hair and wherein the hair coloring mixture comprises:

(a) an oxidising agent; and
(b) an oxidative hair coloring agent;

wherein the combined mixture of (a) and (b) has a pH in the range of from about 1 to about 6 and wherein the resultant color delivered to the hair (Delta E), after at least about 1 month of storage at room temperature, is up to about 75%, preferably up to about 85%, more preferably up to about 90% and most preferably up to about 95% of the total color delivered to the hair (Delta E) from a mixture of (a) and (b) on first application.

According to a further aspect of the present invention there is provided a method for coloring hair wherein the coloring mixture is present in a single package suitable for direct application to the hair and wherein the hair coloring mixture comprises:

(a) an oxidising agent; and (b) an oxidative hair coloring agent;

wherein the combined mixture of (a) and (b) has a pH in the range of from about 1 to about 5 and wherein the resultant color delivered to the hair (Delta E), after at least about 1 month of storage at room temperature, is up to about 75%, preferably up to about 85%, more preferably up to about 90% and most preferably up to about 95% of the total color delivered to the hair (Delta E) from a mixture of (a) and (b) on mixing.

DETAILED DESCRIPTION OF THE INVENTION

As used herein the term 'hair' to be treated may be 'living' i.e. on a living body or may be 'non-living' i.e. in a wig, hairpiece or other aggregation of non-living fibres, such as those used in textiles or fabrics. Mammalian, preferably human hair is preferred. However wool, fur and other melanin containing fibres are suitable substrates for the compositions according to the present invention.

As used herein the term 'hair coloring composition' is used in the broad sense in that it is intended to encompass compositions containing the combinations herein of a low pH (from about 1 to about 6) mixture of oxidising agent and an oxidative coloring agent. Moreover, it is also intended to include complex compositions which contain other components which may or may not be active ingredients. Thus, the term 'hair coloring composition' is intended to apply to compositions which contain, in addition to a mixture of active oxidising agents and oxidative coloring agents, such things as, by way of example, oxidising aids, sequestrants, stabilisers, thickeners, buffers, carriers, surfactants, solvents, antioxidants, polymers, non-oxidative dyes and conditioners.

As discussed above, the low pH, singly packaged, storage stable and/or re-usable hair coloring compositions according to the present invention comprise an oxidising agent (a), which is packaged in combination with an oxidative hair coloring agent (b) wherein the combined mixture of (a) and (b) is storage stable in the pH range of from about 1 to about 5. Preferably the pH of the combined mixture of (a) and (b) is in the range of from about 1.5 to about 5, more preferably from about 1.8 to about 4.7, most preferably from about 2.5 to about 4.5 and especially from about 2.7 to to about 3.8.

The Dye Oxidisation and Hair Coloring Processes

It is understood by those familiar in the art that to successfully color human or animal hair with oxidative dyes it is generally necessary to treat the hair with a mixture of oxidising agent and oxidative hair coloring agent. As herein before discussed the most common oxidising agent is hydrogen peroxide.

Hydrogen peroxide has a pKa in the range of from about 11.2 to about 11.6, and, as such is generally understood to be most effective as a dye oxidising agent at pHs in the range of from about 9 to about 12.

Surprisingly, it has now been found that, at low pH, storage stable and/or re-usable oxidative hair coloring compositions can be developed. Furthermore, it has also been found that improved hair coloring characteristics, such as, initial color development, and improved color washfastness, are provided by the low pH, singly packaged, storage stable and/or re-usable oxidative hair coloring compositions of the present invention, at pHs in the range of from about pH 1 to about pH 6, preferably from about pH 1.5 to about pH 5.8, more preferably from pH 1.5 to about pH 5.5, most preferably from about pH 2 to about pH 5, and especially from about pH 2.5 to about pH 4.5.

Color Stable Singly Packaged Low pH Storage Stable Compositions

The singly packaged hair coloring compositions according to the present invention comprise as an essential feature a mixture of an oxidising agent and an oxidative hair coloring agent at a low pH in the range of from about pH 1 to about pH 5.

As hereinbefore described the singly packaged combined mixture of oxidising and coloring components of the hair coloring compositions according to the present invention have improved storage stability under low pH conditions (about pH 1 to about pH 5) versus conventional, high pH, coloring compositions.

Storage stable singly packaged hair coloring composition, as defined herein, means, single component coloring compositions which are suitable for direct application to the hair which comprise a pre-mixed combination of an oxidising agent and an oxidative hair coloring agent, wherein the coloring composition retains the ability to develop a consistent/predictable initial hair color both imediately after either first formulation (creation of the pre-mix) or on purchase and, after storage over time.

In terms of consumer perception, consistent/predictable initial color, means, that the color delivered to the hair, by the stored composition (Delta E stored), is not visibly different from the color delivered by the composition on first application (first application after purchse). Both initial hair coloring and hair coloring after storage, as will be explained in detail hereinafter, can be measured in terms of Delta E (Delta E target, Delta E stored). Retained color development potential, as defined herein, means, that the color developed by the hair coloring composition on first application (Delta E target) is substantially delivered to the hair after extended storage of the composition over time.

In compositions according to the present invention the color delivered to the hair after at least about 1 hour (60 minutes) of storage (Delta E stored) at room temperature (25° C.) is greater than about 75%, preferably greater than about 80%, more preferably greater than about 85%, most preferably greater than about 90% and especially greater than about 95% of the color delivered to the hair on first application (Delta E target).

In preferred compositions according to the present invention the color delivered to the hair at least about 1 day (24 hours) of storage (Delta E stored) at room temperature (25° C.) is greater than about 75%, preferably greater than about 80%, more preferably greater than about 85%, most preferably greater than about 90% and especially greater than about 95% of the color delivered to the hair on first application (Delta E target).

In highly preferred compositions according to the present invention the color delivered to the hair after at least about 1 month (720 hours) of storage (Delta E stored) at room temperature (25° C.) is greater than about 75%, preferably greater than about 80%, more preferably greater than about 85%, most preferably greater than about 90% and especially greater than about 95% of the color delivered to the hair on first application (Delta E target).

According to one aspect of the present invention, there is provided a singly packaged, storage stable, re-usable hair coloring composition comprising:

(a) an oxidising agent; and (b) an oxidative hair coloring agent;

wherein the combined mixture of (a) and (b) has a pH in the range of from about 1 to about 5 and wherein the mixture of (a) and (b) is capable of being stored at low pH, for at least 1 about month and wherein the resultant color delivered to the hair (Delta E storage) is greater than about 75%, preferably greater than about 85%, more preferably greater than about 90% and most preferably greater than about 95% of the total color delivered to the hair (Delta E target) from a mixture of (a) and (b) on first application.

It is generally accepted that the pH within the hair shaft, of human hair, is around pH 5.5 to pH 6 (C. R. Robbins, Chemical and Physical Behaviour of Human Hair, 2nd Ed. pI57) and that human hair has an inherent buffering capacity. It is known that certain oxidising agents, such as hydrogen peroxide, are storage stable at about pH 4. While not wishing to be bound to any particular theory, it is believed that at pHs in the range of from about 1 to about 5, preferably in the range of from about 1.5 to about 5, more preferably from about 1.8 to about 4.7, most preferably from about 2.5 to about 4.5 and especially from about 2.7 to to about 3.8, the rate of oxidative coupling, between the oxidising agent and the oxidative hair coloring agents is relatively slow. As such, it is proposed herein that, at low pH, mixtures of oxidative hair coloring agents and oxidising agents can be stored stably without significant impact on the color development potential of the resultant hair coloring composition.

The singly packaged, re-usable, low pH oxidative hair coloring compositions of the present invention are also suitable for use in a multi-application format (i.e. the consumer can use a single package for several color applications over a period of time) which give the consumer the ability to re-use the mixed coloring composition for, correction of mistakes, touching up or root coverage, future re-coloring of the hair with the same product/color and/or strand tests on small areas of hair. Singly packaged, as defined herein, means, a hair coloring composition comprising a single packaging component which contains therein oxidising agent and oxidative coloring agent together in a stable, low pH mixture.

Component Parts of Hair Coloring Compositions

As detailed hereinbefore it has been found that oxidative hair coloring materials can be stored at low pH with excellent retained color development potential. As defined herein, retained coloring potential for the oxidative coloring component (b), means, that the color as developed, on mixing the oxidative hair coloring component (b) with the oxidising agent (a), at time zero (i.e. Delta E target), is approximately equivalent to the color as developed from the mixture of the oxidative hair coloring component (b) with the oxidising agent (a), after a period of storage (Delta E stored) at room temperature, 25° C., for X hours.

In preferred storage stable, low pH, singly packaged coloring compositions according to the present invention Delta E (X hours) is greater than about 90%, preferably greater than about 93%, more preferably greater than about 95% and most preferably greater than about 98% of Delta E (target).

Thus according to another aspect of the present invention there is provided a singly packaged, low pH, storage stable, re-usable hair coloring composition comprising:

(a) an oxidising agent; and (b) an oxidative hair coloring agent;

wherein the combined mixture of (a) and (b) has a pH in the range of from about 1 to about 5 and wherein the mixture of(a) and (b) is capable of being stored at low pH, at room temperature (about 25° C.), for at least about 1 month and wherein the color potential delivered to the hair (Delta E) is greater than about 75%, preferably greater than about 85%, more preferably greater than about 90% and most preferably greater than about 95% of the total color delivered to the hair (Delta E) from a mixture of (a) and (b) on first application.

Oxidising Agents

The compositions of the invention comprise as an essential feature at least one oxidising agent. The oxidising agent should be safe and effective for use in the compositions herein. Preferably, the oxidising agents suitable for use herein will be soluble in the compositions according to the present invention when in liquid form and/or in the form intended to be used. Preferably, oxidising agents suitable for use herein will be water-soluble. Water soluble oxidising agents as defined herein means agents which have a solubility to the extent of about 10 g in 1000 ml of deionised water at 25° C. ("Chemistry" C. E. Mortimer. 5th Edn. p277).

Suitable oxidising agents for use herein are selected from inorganic peroxygen oxidising agents, preformed organic peroxyacid oxidising agents and organic peroxide oxidising agents or mixtures thereof.

Inorganic Oxidising Agents

The compositions of the invention may comprise at least one inorganic oxidising agent (hereinafter called 'inorganic peroxygen oxidising agent').

The inorganic peroxygen oxidising agent should be safe and effective for use in the compositions herein. Preferably, the inorganic peroxygen oxidising agents suitable for use herein will be soluble in the compositions according to the present invention when in liquid form and/or in the form intended to be used. Preferably, inorganic peroxygen oxidising agents suitable for use herein will be water-soluble. Water soluble inorganic peroxygen oxidising agents as defined herein means agents which have a solubility to the extent of about 10 g in 1000 ml of deionised water at 25° C. ("Chemistry" C. E. Mortimer. 5th Edn. p277).

The inorganic peroxygen oxidising agents useful herein are generally inorganic peroxygen materials capable of yielding peroxide in an aqueous solution. Inorganic peroxygen oxidising agents are well known in the art and include hydrogen peroxide, inorganic alkali metal peroxides such as sodium periodate, sodium perbromate and sodium peroxide, and inorganic perhydrate salt oxidising compounds, such as the alkali metal salts of perborates, percarbonates, perphosphates, persilicates, persulphates and the like. These inorganic perhydrate salts may be incorporated as monohydrates, tetrahydrates etc. Mixtures of two or more of such inorganic peroxygen oxidising agents can be used if desired. While alkali metal bromates and iodates are suitable for use herein the bromates are preferred. Highly preferred for use in the compositions according to the present invention is hydrogen peroxide.

It has also been found that, under the low pH conditions according to the present invention, it is possible to deliver both improved initial color development, color consistency, washfastness and color intensity versus conventional, high pH, systems (using equivalent levels of peroxide and dyes)

and also equivalent color development (detailed hereinafter in the Experimental Data section in terms of Delta E) versus conventional systems at high pH, while using substantially less oxidising agent (up to 75% less) as well as delivering equivalent color development versus conventional, high pH, systems while using substantially less oxidative hair coloring agent (up to 50% less). Thus, the storage stable and/or re-usable, low pH, hair coloring compositions according to the present invention can be formulated to reduce the level of damage to the hair and levels of skin irritation and staining. Furthermore, as the storage stable and/or re-usable, low pH, hair coloring compositions according to the present invention can be formulated without ammonia there are no ammonia related odor or skin irritation negatives associated with these compositions.

The inorganic peroxygen oxidising agent where present, is present in the compositions according to the present invention at a molar level of from about 0.0003 moles (per 100 g of composition) to less than about 0.2 moles (per 100 g of composition), preferably, the inorganic peroxygen oxidising agent is present at a molar level of from about 0.003 moles to about 0.15 moles, more preferably from about 0.006 moles to about 0.1 moles, and especially from about 0.05 moles to about 0.09 moles (per 100 g of composition).

The inorganic peroxygen oxidising agent, where present, is present in the compositions of the present invention at a level of from about 0.01% to about 1%, preferably from about 0.01% to about 0.8%, more preferably from about 0.01% to about 0.75%, most preferably from about 0.01% to about 0.55% and especially from about 0.01% to about 0.5% by weight.

Preformed Organic Peroxyacid

The compositions according to the present invention may contain one or more preformed organic peroxyacid oxidising agents.

Suitable organic peroxyacid oxidising agents for use in the coloring compositions according to the present invention have the general formula:

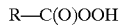

wherein R is selected from saturated or unsaturated, substituted or unsubstituted, straight or branched chain, alkyl, aryl or alkaryl groups with from 1 to 14 carbon atoms.

A class of organic peroxyacid compounds suitable for use herein are the amide substituted compounds of the following general formulae:

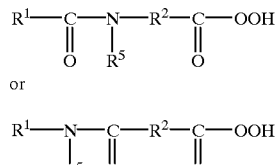

wherein $R^1$ is, a saturated or unsaturated alkyl or alkaryl group, or an aryl group, having from 1 to 14 carbon atoms, $R^2$ is, a saturated or unsaturated alkyl or alkaryl group, or an aryl group, having from 1 to 14 carbon atoms, and $R^5$ is H or, a saturated or unsaturated alkyl or alkaryl group, or an aryl group, having from 1 to 10 carbon atoms. Amide substituted organic peroxyacid compounds of this type are described in EP-A-0,170,386.

Other suitable organic peroxyacid oxidising agents include peracetic, pernanoic, nonylamidoperoxycaproic acid (NAPCA), perbenzoic, m-chloroperbenzoic, di-peroxyisophthalic, mono-peroxyphthalic, peroxylauric, hexanesulphonyl peroxy propionic, N,N-phthaloylamino peroxycaproic, monoper succinic, nonanoyloxybenzoic, dodecanedioyl-monoperoxybenzoic, nonylamide of peroxyadipic acid, diacyl and tetraacylperoxides, especially diperoxydodecanedioic acid, diperoxytetradecanedioic acid and diperoxyhexadecanedioic acid and derivatives thereof. Mono- and diperazelaic acid, mono- and diperbrassylic acid and N-phthaloylaminoperoxicaproic acid and derivatives thereof are also suitable for use herein.

The preferred peroxyacid materials suitable for use herein are selected from peracetic and pernanoic acids and mixtures thereof.

The preformed organic peroxyacid oxidising agents should be safe and effective for use in the compositions herein. Preferably, the preformed organic peroxyacid oxidising agents suitable for use herein will be soluble in the compositions according to the present invention when in liquid form and/or in the form intended to be used. Preferably, preformed organic peroxyacid oxidising agents suitable for use herein will be water-soluble. Water soluble preformed organic peroxyacid oxidising agents as defined herein means agents which have a solubility to the extent of about 10 g in 1000 ml of deionised water at 25° C. ("Chemistry" C. E. Mortimer. 5th Edn. p277).

The preformed organic peroxyacid oxidising agent, where present, is present at a molar level of from about 0.00013 moles to about 0.105 moles (per 100 g) of composition), more preferably from about 0.0013 moles to about 0.05 moles, most preferably from about 0.002 moles to about 0.04 moles and especially from about 0.004 moles to about 0.03 moles (per 100 g) of the hair coloring compositions according to the present invention.

The preformed organic peroxyacid oxidising agent is preferably present at a level of from about 0.01% to about 8%, more preferably from about 0.1% to about 6%, most preferably from about 0.2% to about 4%, and especially from about 0.3% to about 3% by weight of the hair coloring composition. The weight ratio of the inorganic peroxygen oxidising agent to the preformed organic peroxy acid is preferably in the range of from about 0.0125:1 to about 500:1, more preferably from about 0.0125:1 to about 50:1.

In addition to preformed organic peroxyacid oxidising agents and the inorganic peroxygen oxidising agents suitable for use herein, the compositions according to the present invention, may, comprise additional organic peroxides such as urea peroxide, melamine peroxide and mixtures thereof. The level of organic peroxide, where present, is from about 0.01% to about 3%, preferably from about 0.01% to about 2%, more preferably from about 0.1% to about 1.5% and most preferably from about 0.2% to about 1% by weight of composition.

Hair Coloring

Once hair has been colored there is a desire for the color to be resistant to fading, as occasioned by the actions of washing (also known as wash fastness), perspiration, hair spray and other exterior factors such as the action of the sun, and further that the color be retained in a consistent manner for a predictable period of time. Additionally damage to the hair that can lead to irregular dye uptake as discussed above, can lead to increased fading of the damaged portions of the hair and consequently, irregular levels of color fade over time. An additional difficulty commonly associated with the dyeing of human hair is the need for dye systems which avoid any adverse effect on the hair and skin of the user, such as brittle hair, or, irritation of the skin, or, staining (coloring) of the skin.

Thus, it would be desirable to develop a hair coloring composition which exhibits reduced fade, provides improved resistance to wash out during a regular cleansing regimen, can deliver substantially consistent hair color results throughout the hair, which has reduced irritant effect on the skin, which has reduced staining on the skin, which has reduced adverse effects on the hair of the user.

It has now been found that the combination of oxidising agent with one or more oxidative hair coloring agents at a pH below the internal pH of hair, between about pH 1 to about pH 5, in hair coloring compositions can deliver excellent initial hair color in combination with improved color and wash fastness of the hair color over time, desirable color saturation and vividness attributes, reduced hair damage, reduced skin irritation, reduced skin staining and more efficient dyeing. Furthermore, it has been found that the efficacy of color development (color change) from the oxidising agent and oxidative hair coloring agents is improved under the low pH conditions of the present invention. In addition, it has been found that the hair coloring compositions according to the present invention can deliver these excellent hair coloring attributes results with minimal hair damage, at low pH (about 1 to about 6).

It is an object of the present invention to provide storage stable, re-usable, low pH hair coloring compositions which deliver the combination of improved hair coloring attributes, such as, longer lasting color (reduced fade), initial color generation, increased color uptake and color consistency across hair types. Hair types as defined herein means hair of varying age and condition i.e. virgin untreated, grey, permed, bleached etc.

It is a still further object of the present invention to provide storage stable, re-usable, low pH hair coloring compositions which have reduced levels of skin irritation and/or skin staining versus conventional high pH systems and which impart minimal damage to the hair fibres and reduced staining of skin in combination with an acceptable odor.

It is a yet further object of the present invention to provide storage stable, re-usable, low pH hair coloring compositions which exhibit increased efficacy (improved color development). Color development as defined herein, means, the change in the hair color, expressed in terms of Delta E, as defined in the Experimental section herein after. It is a yet further object of the present invention to provide coloring compositions with reduced damage to the skin and/or hair which can deliver equivalent color development (versus conventional high pH systems) in combination with improved washfastness and color consistency while using less dye and/or less of the oxidising agent.

Hair Coloring Agents

The low pH hair coloring compositions of the present invention include as an essential feature an oxidative hair coloring agent. Such oxidative hair coloring agents are used in combination with the oxidising systems of the present invention to formulate permanent, demi-permanent, semi-permanent or temporary hair dye compositions at low pH.

Permanent hair dye compositions as defined herein are compositions which once applied to the hair are substantially resistant to wash-out. Demi-permanent hair dye compositions as defined herein are compositions which are substantially removed from the hair after up to 24 washes. Semi-permnanent hair dye compositions as defined herein are compositions which once applied to the hair are substantially removed from the hair after up to 10 washes. Temporary hair dye compositions as defined herein are compositions which once applied to the hair are substantially removed from the hair after up to 2 washes. These different types of hair coloring compositions can be formulated via the specific combination of oxidant and/or dyes at different levels and ratios. Wash out as defined herein is the process by which hair color is removed from the hair over time during normal hair cleansing regimen. Washfastness as defined herein, means, the resistance of the dyed hair to wash out. Washfastness, as defined herein, can be measured in terms of the relative color change in the dyed hair (Delta E) over several washes (shampoos). Substantial removal of dye from the hair as defined herein means the color change in the dyed hair (Delta E) is greater than about 2 after up to 10 washes.

The concentration of each oxidative hair coloring agent in the low pH coloring compositions according to the present invention is from about 0.001% to about 3% by weight and is preferably from about 0.01% to about 2% by weight.

The total combined level of oxidative hair coloring agents in the compositions according to the present invention is from about 0.001% to about 5%, preferably from about 0.01% to about 4%, more preferably from about 0.1% to about 3%, most preferably from about 0.1% to about 1% by weight.

Typically, in conventional hair coloring compositions the total level of oxidative hair coloring agents present in the composition is in the range of from about 0.2% to about 3.5% by weight. Accordingly, the compositions according to the present invention can display improved hair coloring attributes, such as initial color development and initial color consistency in combination with improved washfastness over time, when compared to conventional, high pH, systems having similar levels of dye. Color consistency, as used herein, means, both the relative predictability of the initial color development and improved color retention over time across different hair types.

The efficacy of the oxidative dyes is improved at low pH such that the compositions of the present invention are valuable for the delivery of good high intensity colors (dark colors) with reduced levels of dye. In particular, good hair coloring results in combination with equivalent color development (versus high pH systems) can be achieved using the inorganic peroxygen oxidising agents of the present invention and substantially less dye versus conventional, high pH, hair coloring compositions.

Thus according to a further aspect of the present invention there is provided a hair coloring composition comprising:
    (a) an oxidising agent;
    (b) an oxidative hair coloring agent; and
    (c) a diluent suitable for application to the hair;
wherein the pH of each of (a) and (b) is in the range of from about 1 to about 6 and wherein the combined mixture of (a) and (b) has a pH in the range of from about 1 to about 5 and wherein both (a) and (b) are capable of being stored at low pH, either separately or once mixed for at least about 1 month at room temperature and wherein the resultant color delivered to the hair (Delta E) is greater than about 75%, preferably greater than about 85%, more preferably greater than about 90% and most preferably greater than about 95% of the total color delivered to the hair (Delta E target) from a mixture of (a) and (b) on mixing.

As herein before described, it has also been found that the combination of oxidising agent with oxidative hair coloring agent at low pH is valuable for the delivery of excellent hair coloring attributes in combination with reduced levels of hair damage, skin irritation and skin staining in combination with an improved odor profile (versus conventional high pH compositions). A further benefit of the low pH coloring compositions according to the present invention is that reduced levels of skin staining can be observed from such compositions, versus conventional, high pH, compositions.

Thus according to a still further aspect of the present invention there is provided a hair coloring composition capable of delivering a light auburn colour to light brown hair having 40% grey comprising:

(a) an oxidising agent;

(b) an oxidative hair coloring agent; and (c) a diluent suitable for application to the hair;

wherein the pH of each of (a) and (b) is in the range of from about 1 to about 5 and wherein the combined mixture of (a) and (b) has a pH in the range of from about 1 to about 6 and wherein both (a) and (b) are capable of being stored at low pH, either separately or once mixed for at least about 1 month at room temperature and wherein the change in level of skin staining after product application (Delta E) is less than about 4, preferably less than about 3, more preferably less than about 2.7. Light brown hair having 40% grey coverage is defined in terms of L, a, b values as having an 'L' value in the range of from about 35 to about 37, an 'a' value in the range of from about 4.5 to about 5.5 and a 'b' value in the range of from about 11.5 to about 12.7.

Without being limited by any particular theory, it is believed that, these improvements (in respect of reduced skin irritation and/or staining) result from the combination of (a) reduced levels of dyes and low pH; (b) the reduction of paraphenylene diamine (PPD) contact sensitisation at low pH (high levels of PPD have been shown to display contact sensitisation at high pH, but not at low pH); (c) the elimination of the formation of nitrobenzene contact sensitisers (which can occur in high pH compositions); (d) reduced levels of skin staining at low pH versus high pH, and; (e) the reduction in skin irritation and odor negatives as a result of the elimination of ammonia and the use of alternative oxidising agents in the low pH dyeing compositions according to the present invention.

Oxidative Hair Coloring Processes

Any oxidative hair coloring agent can be used in the compositions according to the present invention. Typically, but without intending to be limited thereby, oxidative hair coloring agents, consist essentially of at least two components, which are collectively referred to as dye forming intermediates (or precursors). Dye forming intermediates can react in the presence of a suitable oxidant to form a colored molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates, which are also known as oxidative dye precursors, are chemical compounds which become activated upon oxidation and can then react with each other and/or with couplers to form colored dye complexes. The secondary intermediates, also known as color modifiers or couplers, are generally colorless molecules which can form colors in the presence of activated precursors/primary intermediates, and are used with other intermediates to generate specific color effects or to stabilise the color.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colorless molecules prior to oxidation.

While not wishing to be bound by any particular theory it is proposed herein that the process by which color is generated from these primary intermediates and secondary coupler compounds generally includes a stepwise sequence whereby the primary intermediate can become activated (by oxidation), and then enjoins with a coupler to give a dimeric, conjugated colored species, which in turn can enjoin with another 'activated' primary intermediate to produce a trimeric conjugated colored molecule.

Chemistry of Oxidative Hair Coloration Across pH

While not wishing to be bound by any particular theory, it is generally understood that conventional oxidative dyeing typically occurs between oxidative precursor molecules, oxidative coupler molecules and a peroxygen oxidising agent at high pH (8–10). Typical precursors include 1,4-disubstituted benzene derivatives and typical couplers include 1,2- or 1,3-disubstituted benzene derivatives.

It is generally accepted that the pH within the hair shaft, of human hair, is around pH 5.5 to pH 6 (C. R. Robbins, Chemical and Physical Behaviour of Human Hair, 2nd Ed. p157) and that the hair has an inherent buffering capacity.

Surprisingly it has now been found that, oxidative hair coloration at pH 5 or less with oxidising agent(s) and oxidative hair coloring agent is valuable for the delivery of excellent initial hair color in combination with improved color and wash fastness of the hair color over time, desirable color saturation and vividness attributes, reduced hair damage, reduced skin irritation, reduced skin staining and more efficient dyeing. Furthermore, it has been found that the efficiency of color development (i.e., increased color change) from the inorganic peroxygen oxidising agents and the oxidative hair coloring agents of the present invention is improved under the low pH conditions according to the present invention. In addition, it has been found that the low pH hair coloring compositions according to the present invention can deliver these excellent hair coloring attributes results with minimal hair damage.

It has also been found that at pH levels of less than pH 5, preferably from about pH 1.5 to 5.8, more preferably from about pH 1.5 to about 5, more preferably from about 1.8 to about 4.7, most preferably from about 2.5 to about 4.5 and especially from about 2.7 to to about 3.8, further improvements in color development are acheived.

Oxidative Dye Precursors

In general terms, oxidative dye primary intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidative primary intermediates capable of forming colored polymers include materials such as aniline, which has a single finctional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Oxidative dyes known in the art can be used in the low pH compositions according to the present invention. A representative list of primary intermediates and secondary couplers suitable for use herein is found in Sagarin, "Cosmetic Science and Technology," Interscience, Special Ed. Vol. 2 pages 308 to 310. It is to be understood that the primary intermediates detailed below are only by way of example and are not intended to limit the compositions and processes herein.

The typical aromatic diamines, polyhydric phenols, amino phenols, and derivatives thereof, described above as primary intermediates can also have additional substituents on the aromatic ring, e.g. halogen, aldehyde, carboxylic acid, nitro, sulfonic acid and substituted and unsubstituted hydrocarbon groups, as well as additional substituents on the amino nitrogen and on the phenolic oxygen, e.g. substituted and unsubstituted alkyl and aryl groups.

Examples of suitable aromatic diamines, amino phenols, polyhydric phenols and derivatives thereof, respectively, are compounds having the general formulas (I), (II) and (III) below:

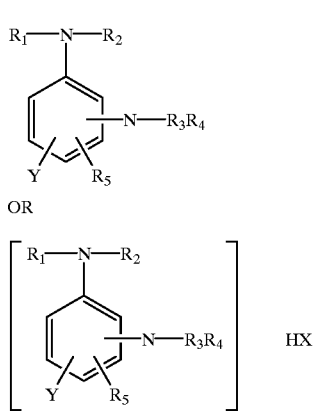

(I)

wherein Y is hydrogen, halogen, (e.g. fluorine, chlorine, bromine or iodine), nitro, amino, hydroxyl,

—COOM or —SO$_3$M (where M is hydrogen or an alkali or alkaline earth metal, ammonium, or substituted ammonium wherein one or more hydrogens on the ammonium ion is replaced with a 1 to 3 carbon atom alkyl or hydroxyalkyl radical), wherein $R_1$, $R_2$, $R_3$ and $R_4$ are the same or different from each other and are selected from the group consisting of hydrogen, $C_1$ to $C_4$ alkyl or alkenyl and $C_6$ to $C_9$ aryl, alkaryl or aralkyl, and $R_5$ is hydrogen, $C_1$ to $C_4$ unsubstituted or substituted alkyl or alkenyl wherein the substituents are selected from those designated as Y, above, or $C_6$ to $C_9$ unsubstituted or substituted aryl, alkaryl or aralkyl wherein the substituents are selected from those defined as Y, above. Since the precursors of formula (I) are amines, they can be used herein in the form of peroxide-compatible salts, as noted, wherein X represents peroxide-compatible anions of the type herein before detailed. The general formula of the salt indicated is to be understood to encompass those salts having mono-, di-, and tri-negative anions.

Specific examples of formula (I) compounds are: o-phenylenediamine, m-phenylenediamine, p-phenylenediamine, 2-chloro-p-phenylenediamine, 2-iodo-p-phenylenediamine, 4-nitro-o-phenylenediamine, 2-nitro-p-phenylenediamine, 1,3,5-triaminobenzene, 2-hydroxy-p-phenylenediamine, 2,4-diaminobenzoic acid, sodium 2,4-diaminobenzoate, calcium di-2,4-diaminobenzoate, ammonium 2,4-diaminobenzoate, trimethylammonium 2,4-, diaminobenzoate, tri-(2-hydroxyethyl)ammonium 2,4- diaminobenzoate, 2,4-diaminobenzaldehyde carbonate, 2,4-diaminobenzensulfonic acid, potassium 2,4-diaminobenzenesulfonate, N,N-diisopropyl-p-, phenylenediamine bicarbonate, N,N-dimethyl-p-phenylenediamine, N-ethyl-N'-(2-propenyl)-p-phenylenediamine, N-phenyl-p-phenylenediamine, N-phenyl-N-benzyl-p-phenylenediamine, N-ethyl-N'-(3-ethylphenyl)-p-phenylenediamine, 2,4-toluenediamine, 2-ethyl-p-phenylenediamine, 2-(2-bromoethyl)-p-phenylenediamine, 2-phenyl-p-phenylenediamine laurate, 4-(2,5-diaminophenyl)benzaldehyde, 2-benzyl-p-phenylenediamine acetate, 2-(4-nitrobenzyl)-p-phenylenediamine, 2-(4-methylphenyl)-p-phenylenediamine, 2-(2,5-diaminophenyl)-5-methylbenzoic acid, methoxyparaphenylenediamine, dimethyl-p-phenylenediamine, 2,5-dimethylpara-phenylenediamine, 2-methyl-5-methoxy-para-phenylenediamine, 2,6-methyl-5-methoxy-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamethyl)aniline, 3-methyl-4-amino-N-ethyl-N-(carbamethyl)aniline, 4-amino-N-ethyl-(β-piperidonoethyl)aniline, 3-methyl-4-amino-N-ethyl-(β-piperidonoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl) aniline, 3-methyl-4-amino-N-ethyl-N-(β-acetylaminoethyl) aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine, N-(4-aminophenyl)piperidine, 2,3-dimethyl-p-phenylenediamine, isopropyl-p-phenylenediamine, N,N-bis-(2-hydroxyethyl)-p-phenylenediamine sulphate.

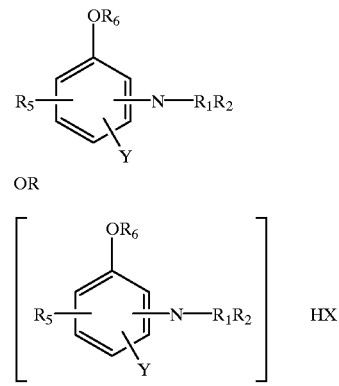

(II)

where X and Y are the same as in formula (I), $R_1$ and $R_2$ can be the same or different from each other and are the same as in formula (I), $R_5$ is the same as in formula (I) and $R_6$ is hydrogen or $C_1$ to $C_4$ substituted or unsubstituted alkyl or alkenyl wherein the substituents are selected from those defined as Y in formula (I).

Specific examples of formula (II) compounds are: o-aminophenol, m-aminophenol, p-aminophenol, 2-iodo-p-aminophenol, 2-nitro-p-aminophenol, 3,4-dihydroxyaniline, 3,4-diaminophenol, chioroacetate, 2-hydroxy-4-aminobenzoic acid, 2-hydroxy-4-aminobenzaldehyde, 3-amino-4-hydroxybenzenesulfonic acid, N,N-diisopropylp-aminophenol, N-methyl-N-(1-propenyl)-p-aminophenol, N-phenyl-N-benzyl-p-aminophenol sulphate, N-methyl-N-(3-ethyrphenyl)-p-aminophenol, 2-nitro-5-ethyl-p-aminophenol, 2-nitro-5-(2-bromoethyl)-p-aminophenol, (2-hydroxy-5 -aminophenyl)acetaldehyde, 2-methyl-p-aminophenol, (2-hydroxy-5-aminophenyl)acetic acid, 3-(2-hydroxy-5-aminophenyl)-1-propene, 3-(2-hydroxy-5-aminophenyl)-2-chloro-1-propene, 2-phenyl-p-aminophenol palmitate, 2-(4-nitropheny 1)-p-aminophenol, 2-benzyl-p-aminophenol, 2-(4-chlorobenzyl-p-aminophenol perchlorate, 2-(4-methylphenyl)-p-aminophenol, 2-(2-amino-4-methylphenyl)-p-aminophenol, p-methoxyaniline, 2-bromoethyl-4-aminophenyl ether phosphate, 2-nitroethyl-4-aminophenyl ether bromide, 2-aminoethyl-4-aminophenyl ether, 2-hydroxyethyl-4-aminophenyl ether, (4-aminophenoxy)acetaldehyde, (4-aminophenoxy)acetic acid, (4-aminophenoxy)methanesulfonic acid, 1-propenyl-4-aminophenyl ether isobutyrate, (2-chloro)-1-propenyl-4-aminophenyl ether, (2-nitro)-1-propenyl-4-aminophenyl ether, (2-amino)-propenyl-4-aminophenyl ether, (2-hydroxy)-1-propenyl-4-aminophenyl ether, N-methyl-p-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 3-hydroxymethyl-4-aminophenol.

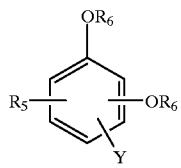

(III)

where Y, $R_5$ and $R_6$ are as defined above in formula (II).

Specific examples of formula (II) compounds are: o-hydroxyphenol (catechol), m-hydroxyphenol (resorcinol), p-hydroxyphenol (hydroquinone), 4-methoxyphenol, 2-methoxyphenol, 4-(2-chloroethoxy)phenol, 4-(2-propenoxy)phenol, 4-(3-chloro-2-propenoxy)phenol, 2-chloro-4-hydroxyphenol (2-chlorohydroquinone), 2-nitro-4-hydroxyphenol(2-nitrohydroquinone), 2-amino-4-hydroxyphenol, 1,2,3-trihydroxybenzene (pyrogallol), 2,4-dihydroxybenzaldehyde, 3,4-dihydoxybenzoic acid, 2,4-dihydroxybenzenesulfonic acid, 3-ethyl-4-hydroxyphenol, 3-(2-nitroethyl)-4-hydroxyphenol, 3-(2-propenyl)-4-hydroxyphenol, 3-(3-chloro-2-propenyl)-4-hydroxyphenol, 2-phenyl-4-hydroxyphenol, 2-(4-chlorophenyl)-4-hydroxyphenol, 2-benzyl-4-hydroxyphenol, 2-(2-nitrophenyl)-4-hydroxyphenol, 2-(2-methylphenyl)-4-hydroxyphenol, 2-(2-methyl-4-chlorophenyt)-4-hydroxyphenol, 3-methoxy-4-hydroxy-benzaldehyde, 2-methoxy-4-(1-propenyl)phenol, 4-hydroxy-3-methoxycinnamic acid, 2,5-dimethoxyaniline, 2-methyiresorcinol, alpha napthol and salts thereof.

Secondary coupling compounds (color modifiers), such as those detailed hereinafter, are preferably used in conjunction with the primnary intermediates herein and are thought to interpose themselves in the colored polymers during their formation and to cause shifts in the electronic spectra thereof, thereby resulting in slight color changes.

Secondary coupling compounds which are suitable for inclusion in the coloring compositions and processes herein before described include certain aromatic amines and phe-nols and derivatives thereof which do not produce color singly, but which modify the color, shade or intensity of the colors developed by the primary oxidized dye intermediates. Certain aromatic amines and phenolic compounds, and derivatives thereof, including some aromatic diamines and polyhydric phenols of the types described by formulas (I), (II) and (III) above, but which are well known in the art not to be suitable primary intermediates, are suitable as couplers herein. Polyhydric alcohols are also suitable for use as couplers herein.

The aromatic amines and phenols and derivatives described above as couplers can also have additional substituents on the aromatic ring, e.g., halogen, aldehyde, carboxylic acid, nitro, sulfonyl and substituted and unsubstituted by hydrocarbon groups, as well as additional substituents on the amino nitrogen, or phenolic oxygen, e.g. substituted and unsubstituted alkyl and aryl groups. Again, peroxide-compatible salts thereof are suitable for use herein.

Examples of aromatic amines, phenols and derivatives thereof are compounds of the general formulas (IV) and (V) below:

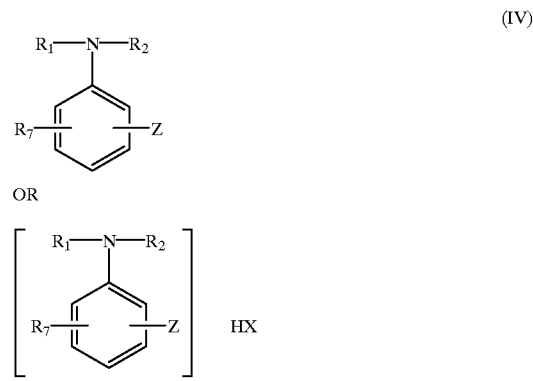

wherein Z is hydrogen, $C_1$ and $C_3$ alkyl, halogen (e.g. fluorine, chlorine, bromine or iodine) nitro,

—COOM or $SO_3M$, (where M is hydrogen or an alkali or alkaline earth metal, ammonium or substituted ammonium wherein one or more hydrogens on the ammonium ion is replaced with a 1 to 3 carbon atom alkyl or hydroxyalkyl radical), wherein $R_1$ and $R_2$ are the same or different and are selected from the group consisting of hydrogen, $C_1$ to $C_4$ alkyl or alkenyl and $C_6$ to $C_9$ aryl, alkaryl or aralkyl and $R_7$ is hydrogen, $C_1$ to $C_4$ unsubstituted or substituted alkyl or alkenyl wherein the substituents are selected from those designated as Z above or $C_6$ to $C_9$ unsubstituted or substituted aryl, alkaryl or aralkyl wherein the substituents are selected from those defined as Z above and wherein X is as defined in formula (I).

Specific examples of formula (IV) compounds are: aniline, p-chloroaniline, p-fluoroaniline, p-nitroaniline, p-aminobenzaldehyde, p-aminobenzoic acid, sodium-p-aminobenzoate, lithium- p-aminobenzoate, calcium di-p-aminobenzoate, ammonium-p-aminobenzoate, trimethylammonium-p-aminobenzoate, tri(2-hydroxyethyl)-p-aminobenzoate, p-aminobenzenesulfonic acid, potassium p-aminobenzenesulfonate, N-methylaniline, N-propyl-N- phenylaniline, N-methyl-N-2-propenylaniline, N-benzylaniline, N-(2-ethylphenyl)aniline, 4-methylaniline, 4-(2-bromoethyl)aniline, 2-(2-nitroethyl)aniline, (4-aminophenyl)acetaldehyde, (4-aminophenyl)acetic acid, 4-(2-propenyl)aniline acetate, 4-(3-bromo-2-propenyl) aniline, 4-phenylaniline chloroacetate, 4-(3-chlorophenyl) aniline, 4-benzylaniline, 4-(4-iodobenzyl)aniline, 4-(3-ethylphenyl)aniline, 4-(2-chloro-4-ethylphenyl)aniline.

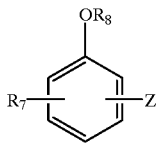

(V)

wherein Z and $R_7$ are defined as in formula (IV) and $R_8$ is hydrogen or $C_1$ to $C_4$ substituted or unsubstituted alkyl or alkenyl wherein the substituents are selected from those defined as Z in formula (IV).

Specific examples of formula (V) compounds are: phenol, p-chlorophenol, p-nitrophenol, p-hydroxybenzaldehyde, p-hydroxybenzoic acid, p-hydroxybenzenesulfonic acid, ethylphenyl ether, 2-chloroethylphenyl ether, 2-nitroethylphenyl ether, phenoxyacetaldehyde, phenoxyacetic acid, 3-phenoxy-1-propene, 3-phenoxy-2-nitro-1-propene, 3-phenoxy-2-bromo-1-propene, 4-propylphenol, 4-(3-bromopropyl)phenol, 2-(2-nitroethyl)phenol, (4-hydroxyphenyl)acetaldehyde, (4-hydroxyphenyl)acetic acid, 4-(2-propenyl)phenol, 4-phenylphenol, 4-benzylphenol, 4-(3-fluoro-2-propenyl)phenol, 4-(4-chlorobenzyl)phenol, 4-(3-ethylphenyl)phenol, 4-(2-chloro-3-ethylphenyl)phenol, 2,5-xylenol, 2,5-diaminopyridine, 2-hydroxy-5-aminopyridine, 2-amino-3-hydroxy pyridine, tetraaminopyrimindine, 1,2,4-trihydroxybenzene, 1,2,4-trihydroxy-5-($C_1$–$C_6$-alkyl)benzene, 1,2,3-trihydroxybenzene, 4-aminoresorcinol, 1,2-dihydroxybenzene, 2-amino-1,4-dihydroxybenzene, 2-amino-4-methoxy-phenol, 2,4-diaminophenol, 3-methoxy- 1,2-dihydroxy-benzene, 1,4-dihydroxy-2-(N,N-diethylamino)benzene, 2,5-diamino-4-methoxy-1-hydroxybenzene, 4,6-dimethoxy-3-amino-1-hydroxybenzene, 2,6-dimethyl-4-[N-(p-hydroxyphenyl) amino]-1-hydroxybenzene, 1,5-diamino-2-methyl-4-[N-(p-hydroxyphenyl)amino]benzene and salts thereof.

Additional primary intermediates suitable for use herein include catechol species and in particular catechol "dopa" species which includes dopa itself as well as homologs, analogs and derivatives of DOPA. Examples of suitable cachetol species include cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group.

In general suitable catechols are represented by formula (VI) below:

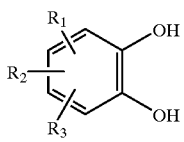

(VI)

wherein $R_1$, $R_2$ and $R_3$, which may be the same or different, are electron donor or acceptor substutuents selected from H, lower ($C_1$–$C_6$) alkyl, OH, OR, COOR, NHCOR, CN, COOH, Halogen, $NO_2$, $CF_3$, $SO_3H$ or $NR_4R_5$, with the proviso that only one of the $R_1$, $R_2$ or $R_3$ can be CN, COOH, halogen, $NO_2$, $CF_3$ or $SO_3H$: $R_4$ and $R_5$, which may be the same or different, are H, lower ($C_1$–$C_6$) alkyl or substituted lower ($C_1$–$C_6$) alkyl in which the substituent may be OH, OR, $NHCOR_6$, $NHCONH_2$, $NHCO_2R_6$, $NHCSNH_2$, CN, COOH, $SO_3H$, $SO_2NR_6$, $SO_2R_6$ or $CO_2R_6$. $R_6$ is lower ($C_1$–$C_6$) alkyl, lower ($C_1$–C6) hydroxyalkyl phenyl linked to the nitrogen by an alkylene chain, phenyl or substituted phenyl with the substituent defined as $R_1$, and R is $C_1$–$C_6$ alkyl or $C_1$–$C_6$ hydroxyalkyl.

Also included herein are oxidative hair coloring agents of the formula:

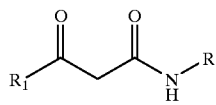

wherein: $R_1$=substituted or unsubstituted benzene ring, tertiary-butyl, etc.; R=substituted or unsubstituted benzene ring and the formula:

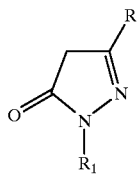

wherein R=aminoalkyl, amidoalkyl, aminobenzene (substituted or unsubstituted), amidobenzene (substituted or unsubstituted), alkyl, substituted or unsubstituted benzene ring; $R_1$=substituted or unsubstituted benzene ring.

The primary intermediates can be used herein alone or in combination with other primary intermediates, and one or more can be used in combination with one or more couplers. The choice of primary intermediates and couplers will be determined by the color, shade and intensity of coloration which is desired. There are nineteen preferred primary intermediates and couplers which can be used herein, singly or in combination, to provide dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxypyridine, 1-napthol, N,N bis(2-hydroxyethyl)p-phenylenediamine, 4-amino-2-hydroxytoluene, 1,5-dihydroxynapthalene, 2-methyl resorcinol and 2,4-diaminoanisole. These can be used in the molecular form or in the form of peroxide-compatible salts, as detailed above.

The primary intermediates and coupling compounds as aforementioned herein may be combined to deliver a wide variety of colors to the hair. The hair colors can vary by both depth of color and intensity of color. As hereinbefore described the compositions according to the present invention are valuable for the provision of high intensity colors. Intensity of color as defined herein means the quantity of color compound formed on and retained in the hair. In general, high intensity as defined herein means dark or deep colors such as dark red, dark brown or black etc. In accordance, with the above it is possible to formulate hair colors of varying color intensity by adjusting the initial levels of each of the oxidative dyeing materials.

For example low intensity colors such as natural blond to light brown hair shades generally comprise from about 0.001% to about 5%, preferably from about 0.1% to about 2%, more preferably from about 0.2% to about 1% by weight of coloring composition of total oxidative dyeing agents and may be achieved by the combination of primary intermediates such as 1,4-diamino-benzene, 2,5-diamino toluene, 2,5-diamino-anisole, 4-aminophenol, 2,5-diamino-benzyl alcohol and 2-(2',5'-diamino)phenyl-ethanol with couplers such as resorcinol, 2-methyl resorcinol or 4-chloro resorcinol.

Similarly combination of the above primary intermediates with couplers, such as, 5-amino-2-methyl phenol and 1,3-diamino-benzene derivatives such as 2,4-diamino-anisole at levels of from about 0.5% to about 1% of total dyeing agents can lead to medium intensity red colors. High intensity colors such as blue to blue-violet hair shades can be produced by the combination of the above primary intermediates with couplers such as 1,3-diamino-benzene or its derivatives such as 2,5-diamino-toluene at levels of from about 1% to about 6% by weight of composition of total dyeing agents. Black hair colors can be obtained by combining the aforementioned primary intermediates with couplers such as 1,3-diaminobenzene or its derivatives However considerations have been raised against the physiological compatibility of para-amino phenol which is commonly used to impart red colors to the hair. Similarly, the physiological compatibility of some of the agents favoured for the production of black color such as paraphenylene diamine (PPD) has been called into question. Thus a need exists for oxidative hair coloring compositions which have an improved safety profile and in particular oxidative hair compositions for the delivery of dark colors i.e. high color intensity dyes, which have an improved safety profile. As discussed herein before, the low pH compositions of the present invention provide excellent hair coloring attributes in combination with reduced levels of hair damage and skin staining and/or irritation.

As such the compositions according to the present invention are valuable for the delivery of improved hair condition attributes in combination with good initial color development and consistency and improved wash fastness over time in addition to having reduced levels of hair damage and skin irritation and/or staining.

Non-oxidative and Other Dyes

The hair coloring compositions of the present invention may, in addition to the essential oxidative hair coloring agents, optionally include non-oxidative and other dye materials. Optional non-oxidative and other dyes suitable for use in the hair coloring compositions and processes according to the present invention include both semi-permanent, temporary and other dyes. Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp250–259); 'The Chemistry and Manufacture of Cosmetics'. Volume IV. 2nd Ed. Maison G. De Navarre at chapter 45 by G. S. Kass (pp841–920); 'cosmetics: Science and Technology' 2nd Ed., Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Direct action dyes which do not require an oxidative effect in order to develop the color, are also designated hair tints and have long been known in the art. They are usually applied to the hair in a base matrix which includes surfactant material. Direct action dyes include nitro dyes such as the derivatives of nitroamino benzene or nitroaminophenol; disperse dyes such as nitroaryl amines, aminoanthraquinones or azo dyes; anthraquinone dyes, naphthoquinone dyes; basic dyes such as Acridine Orange C.I. 46005.

Nitrodyes are added to dyeing compositions to enhance colour of colorant and to add suitable aesthetic colour to the dye mixture prior to application.

Further examples of direct action dyes include the Arianor dyes basic brown 17, C.I.(color index)—no. 12,251; basic red 76, C.I.—12,245; basic brown 16, C.I.—12,250; basic yellow 57, C.I.—12,719 and basic blue 99, C.I.—56,059 and further direct action dyes such as acid yellow 1, C.I.—10, 316 (D&C yellow no.7); acid yellow 9, C.I.—13,015; basic violet C.I.—45,170; disperse yellow 3, C.I.—11,855; basic yellow 57, C.I.—12,719; disperse yellow 1, C.I.—10,345; basic violet 1, C.I.—42,535, basic violet 3, C.I.—42,555; greenish blue, C.I.—42090 (FD&C Blue no.1); yellowish red, C.I.—14700 (FD&C red no.4); yellow, C.I.19140 (FD&C yellow no5); yellowish orange, C.I.15985 (FD&C yellow no.6); bluish green, C.I.42053 (FD&C green no.3); yellowish red, C.I.16035 (FD&C red no.40); bluish green, C.I.61570 (D&C green no.3); orange, C.I.45370 (D&C orange no.5); red, C.I.15850 (D&C red no.6); bluish red, C.I.15850(D&C red no.7); slight bluish red, C.I.45380 (D&C red no.22); bluish red, C.I.45410(D&C red no.28); bluish red, C.I.73360(D&C red no.30); reddish purple, C.I.17200(D&C red no.33); dirty blue red, C.I.15880(D&C red no.34); bright yellow red, C.I.12085(D&C red no.36); bright orange, C.I.15510(D&C orange no.4); greenish yellow, C.I.47005(D&C yellow no.10); bluish green, C.I.59040(D&C green no.8); bluish violet, C.I.60730(Ext. D&C violet no.2); greenish yellow, C.I.10316(Ext. D&C yellow no.7);

Fibre reactive dyes include the Procion (RTM), Drimarene (RTM), Cibacron (RTM), Levafix (RTM) and Remazol (RTM) dyes available from ICI, Sandoz, Ciba-Geigy, Bayer and Hoechst respectively.

Natural dyes and vegetable dyes as defined herein include henna (Lawsonia alba), camomile (Matricaria chamomila or Anthemis nobilis), indigo, logwood and walnut hull extract.

Temporary hair dyes, or hair coloring rinses, are generally comprised of dye molecules which are too large to diffuse into the hair shaft and which act on the exterior of the hair. They are usually applied via a leave-in procedure in which the dye solution is allowed to dry on the hair surface. As such these dyes are typically less resistant to the effects of washing and cleaning the hair with surface active agents and are washed off of the hair with relative ease. Any temporary hair dye may suitably be used in the compositions of the invention and examples of preferred temporary hair dyes are illustrated below.

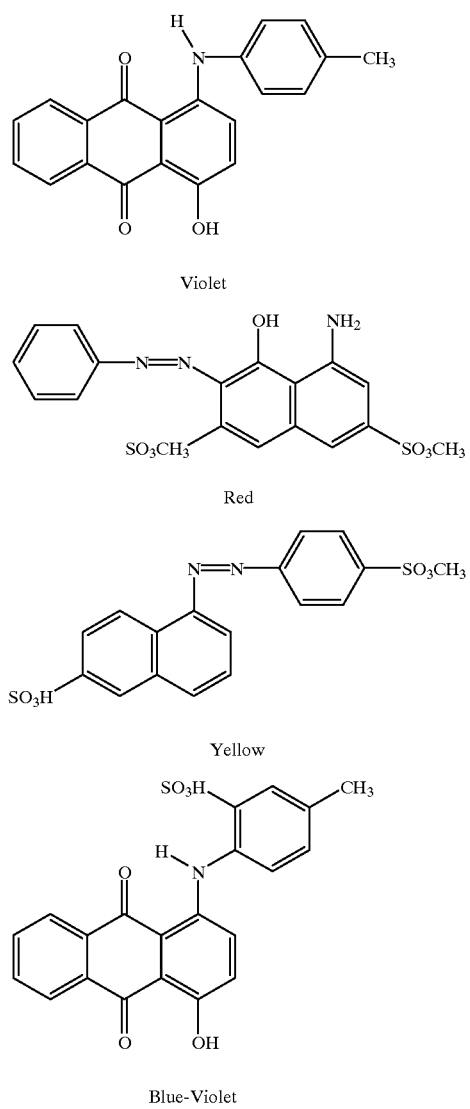

Violet

Red

Yellow

Blue-Violet

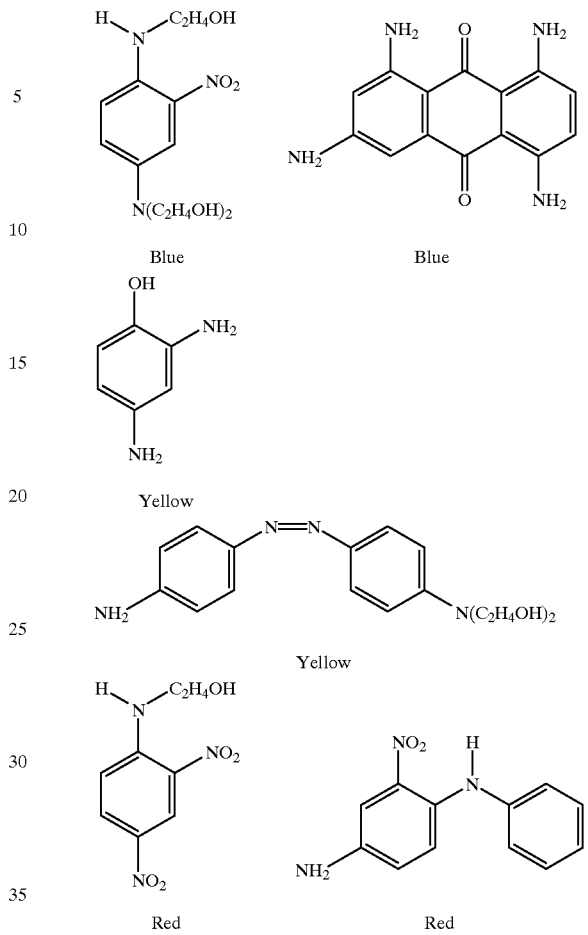

Blue

Blue

Yellow

Yellow

Red

Red

Semi-permanent hair dyes are dyes which are generally smaller in size and effect to temporary hair rinses but are generally larger than permanent (oxidative) dyes. Typically, semi-permanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process and in general semi-permanent dyes are largely washed out of the hair after about 5 to 8 washes. Any semi-permanent dye system may be suitably used in the compositions of the present invention. Suitable semi-permanent dyes for use in the compositions of the present invention are HC Blue 2, HC Yellow 4, HC Red 3, Disperse Violet 4, Disperse Black 9, HC Blue 7, HC Yellow 2, Disperse Blue 3, Disperse violet 1 and mixtures thereof. Examples of semi-permanent dyes are illustrated below:

Typical semi-permanent dye systems incorporate mixtures of both large and small color molecules. As the size of the hair is not uniform from root to tip the small molecules will diffuse both at the root and tip, but will not be retained within the tip, while the larger molecules will be generally only be able to diffuse into the ends of the hair. This combination of dye molecule size is used to help give consistent color results from the root to the tip of the hair both during the initial dyeing process and during subsequent washing.

Buffering Agents

The coloring compositions of the present invention have a pH in the range of from about 1 to about 5, preferably 1.5 to about 5, more preferably from about 1.8 to about 4.7, most preferably from about 2.5 to about 4.5 and especially from about 2.7 to to about 3.8.

As herein before described the pH of the preferred coloring compositions of the present invention are maintained within the desired pH range via the action of the inorganic peroxygen oxidising agent. However, if so desired, the compositions may contain one or more optional buffering agents and/or hair swelling agents (HSAs). Several different pH modifiers can be used to adjust the pH of the final composition or any constituent part thereof.

This pH adjustment can be effected by using well known acidifying agents in the field of treating keratinous fibres, and in particular human hair, such as inorganic and organic acids such as hydrochloric acid, tartaric acid, citric acid, succinic acid, phosphoric acid and carboxylic or sulphonic acids such as ascorbic acid, acetic acid, lactic acid, sulphuric acid, formic acid, ammonium sulphate and sodium dihydrogenphosphate/phosphoric acid, disodium hydrogenphosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid, succinic acid and mixtures thereof.

Examples of alkaline buffering agents are ammonium hydroxide, ethylamine, dipropylamine, triethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-argenine, lysine, alanine, leucine, iso-leucine, oxylysine and histidine and alkanolamines such as dimethylaminoethanol and aminoalkylpropanediol and mixtures thereof. Also suitable for use herein are compounds that form $HCO_3^-$ by dissociation in water (hereinafter referred to as 'ion forming compounds'). Examples of suitable ion forming compounds are $Na_2CO_3$, $NaHCO_3$, $K_2CO_3$, $(NH4)_2CO_3$, $NH_4HCO_3$, $CaCO_3$ and $Ca(HCO_3)$ and mixtures thereof.

Preferred for use herein as buffering agents are organic and inorganic acids having a first pKa below about pH 6, and their conjugate bases. As defined herein, first pKa means, the negative logarithm (to the base 10) of the equilibrium constant, K, where K is the acid dissociation constant. Suitable organic and inorganic acids for use herein are: aspartic, maleic, tartaric, glutamic, glycolic, acetic, succinic, salycilic, formic, benzoic, malic, lactic, malonic, oxalic, citric, phosphoric acid and mixtures thereof. Particularly preferred are acetic, succinic, salycilic and phosphoric acids and mixtures thereof.

The low pH coloring compositions according to the present invention, when a form of intended use, may, as will be described later herein, may be comprised of a final solution containing both oxidising agent and an oxidative hair coloring agent which have been admixed prior to application to the hair or a single component system. Additional, optional materials may be present either in combination with the oxidising agent/coloring agent mixture or as separately packaged units. As such, the compositions according to the present invention may comprise coloring kits of a number of separate components.

In oxidising and coloring kits comprising a portion of inorganic peroxygen oxidising agent, which may be present in either solid or liquid form, such as hydrogen peroxide, a buffering agent solution can be used to stabilise hydrogen peroxide. Since hydrogen peroxide is stable in the pH range from 2 to 4, it is necessary to use a buffering agent having a pH within this range. Dilute acids are suitable hydrogen peroxide buffering agents.

In oxidising and coloring kits comprising an oxidising agent (which may be in solid or liquid form) in combination with one or more coloring agents, a buffering agent capable of maintaining a solution pH in the range of from about 1 to about 5, preferably from about 1.5 to about 5, more preferably from about 1.8 to about 4.7, most preferably from about 2.5 to about 4.5 and especially from about 2.7 to to about 3.8. As such it is necessary to use a buffering agent having a pH within this range.

Catalyst

The coloring compositions herein may optionally contain a transition metal containing catalyst for the peroxygen oxidising agents and the, optional, preformed peroxy acid oxidising agent(s). One suitable type of catalyst is a catalyst system comprising a heavy metal cation of defined bleach catalytic activity, such as copper, iron or manganese cations, an auxiliary metal cation having little or no bleach catalytic activity, such as zinc or aluminium cations, and a sequestrant having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

Other types of suitable catalysts include the manganese-based complexes disclosed in U.S. Pat. Nos. 5,246,621 and 5,244,594. Preferred examples of these catalysts include $Mn^{IV}_2(u-O)_3(1,4,7\text{-trimethyl-}1,4,7\text{-triazacyclononane})_2\text{-}(PF_6)_2$, $Mn^{III}_2(u-O)_1(u-OAc)_2(1,4,7\text{-trimethyl-}1,4,7\text{-triazacyclononane})_2\text{-}(ClO_4)_2$, $Mn^{IV}_4(u-O)_6(1,4,7\text{-triazacyclononane})_4\text{-}(ClO_4)_2$, $Mn^{III}Mn^{IV}_4(u-O)_1(u-OAc)_2\text{-}(1,4,7\text{-trimethyl-}1,4,7\text{-triazacyclononane})_2\text{-}(ClO_4)_3$, and mixtures thereof. Others are described in EP-A-0,549,272. Other ligands suitable for use herein include 1,5,9-trimethyl-1,5,9-triazacyclododecane, 2-methyl-1,4,7-triazacyclononane, 2-methyl-1,4,7-triazacyclononane, 1,2,4,7-tetramethyl-1,4,7-triazacyclononane, and mixtures thereof.

For examples of suitable catalysts see U.S. Pat. Nos. 4,246,612 and 5,227,084. See also U.S. Pat. No. 5,194,416 which teaches mononuclear manganese (IV) complexes such as $Mn(1,4,7\text{-trimethyl-}1,4,7\text{-triazacyclononane})(OCH_3)_3\text{-}(PF_6)$. Still another type of suitably catalyst, as disclosed in U.S. Pat. No. 5,114,606, is a water-soluble complex of manganese (III), and/or (IV) with a ligand which is a non-carboxylate polyhydroxy compound having at least three consecutive C—OH groups. Other examples include binuclear Mn complexed with tetra-N-dentate and bi-N-dentate ligands, including $N_4Mn^{III}(u-O)_2Mn^{IV}N_4)^+$ and $[Bipy_2Mn^{III}(u-O)_2Mn^{IV}bipy_2]\text{-}(ClO_4)_3$.

Further suitable catalysts are described, for example, in EP-A-0,408,131 (cobalt complex catalysts), EP-A-0,384,503, and EP-A-0,306,089 (metallo-porphyrin catalysts), U.S. Pat. No. 4,728,455 (manganese/multidentate ligand catalyst), U.S. Pat. No. 4,711,748 and EP-A-0,224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), DE-A-2,054,019 (cobalt chelant catalyst) CA-A-866,191 (transition metal-containing salts), U.S. Pat. No. 4,430,243 (chelants with manganese cations and non-catalytic metal cations), and U.S. Pat. No. 4,728,455 (manganese gluconate catalysts).

Heavy Metal Ion Sequestrant

The coloring compositions of the invention may contain as an optional component a heavy metal ion sequestrant. By heavy metal ion sequestrant it is meant herein components which act to sequester (chelate or scavenge) heavy metal ions. These components may also have calcium and magnesium chelation capacity, but preferentially they show selectivity to binding heavy metal ions such as iron, manganese and copper. Such sequestering agents are valuable in hair coloring compositions as herein described for the delivery of controlled oxidising action as well as for the provision of good storage stability of the hair coloring products.

Heavy metal ion sequestrants are generally present at a level of from about 0.005% to about 20%, preferably from about 0.01% to about 10%, more preferably from about 0.05% to about 2% by weight of the compositions.

Various sequestering agents, including the amino phosphonates, available as Dequest (RTM) from Monsanto, the nitriloacetates, the hydroxyethyl-ethylene triamines and the like are known for such use. Suitable heavy metal ion sequestrants for use herein include organic phosphonates, such as the amino alkylene poly (alkylene phosphonates), alkali metal ethane 1-hydroxy disphosphonates and nitrilo trimethylene phosphonates.

Preferred among the above species are diethylene triamine penta (methylene phosphonate), ethylene diamine tri (methylene phosphonate) hexamethylene diamine tetra (methylene phosphonate) and hydroxy-ethylene 1,1 diphosphonate.

Preferred biodegradable non-phosphorous heavy metal ion sequestrants suitable for use herein include nitrilotriacetic acid and polyaminocarboxylic acids such as ethylenediaminotetracetic acid, ethylenetriamine pentaacetic acid, ethylenediamine disuccinic acid, ethylenediamine diglutaric acid, 2-hydroxypropylenediamine disuccinic acid or any salts thereof. Especially preferred is ethylenediamine-N,N'-disuccinic acid (EDDS). see U.S. Pat. No. 4,704,233, or the alkali metal, alkaline earth metal, ammonium, or substituted ammonium salts thereof, or mixtures thereof.

Other suitable heavy metal ion sequestrants for use herein are iminodiacetic acid derivatives such as 2-hydroxyethyl diacetic acid or glyceryl imino diacetic acid, described in EP-A-317,542 and EP-A-399,133. The iminodiacetic acid-N-2-hydroxypropyl sulfonic acid and aspartic acid N-carboxymethyl N-2-hydroxypropyl-3-sulfonic acid sequestrants described in EP-A-516,102 are also suitable herein. The β-alanine-N,N'-diacetic acid, aspartic acid-N,N'-diacetic acid, aspartic acid-N-monoacetic acid and iminodisuccinic acid sequestrants described in EP-A-509,382 are also suitable.

EP-A-476,257 describes suitable amino based sequestrants. EP-A-510,331 describes suitable sequestrants derived from collagen, keratin or casein. EP-A-528,859 describes a suitable alkyl iminodiacetic acid sequestrant. Dipicolinic acid and 2-phosphonobutane-1,2,4-tricarboxylic acid are also suitable. Glycinamide-N,N'-disuccinic acid (GADS), ethylenediamine-N-N'-digulataric acid (EDDG) and 2-hydroxypropylenediamine-N-N'-disuccinic acid (HPDDS) are also suitable.

The heavy metal ion sequestering agents of the present invention may be used in their alkali or alkaline earth metal salts.

Thickeners

The coloring compositions of the present invention may additionally include a thickener at a level of from about 0.05% to about 20%, preferably from about 0.1% to about 10%, more preferably from about 0.5% to about 5% by weight. Thickening agents suitable for use in the compositions herein are selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer which are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Diluent

Water is the preferred diluent for the compositions according to the present invention. However, the compositions according to the present invention may include one or more solvents as additional diluent materials. Generally, solvents suitable for use in the coloring compositions of the present invention are selected to be miscible with water and innocuous to the skin. Solvents suitable for use as additional diluents herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. Water is the preferred principal diluent in the compositions according to the present invention. Principal diluent, as defined herein, means, that the level of water present is higher than the total level of any other diluents.

The diluent is present at a level preferably of from about 5% to about 99.98%, preferably from about 15% to about 99.5%, more preferably at least from about 30% to about 99%, and especially from about 50% to about 98% by weight of the compositions herein.

Enzyme

A further additional material useful in the hair coloring compositions according to the present invention is one or more enzymes.

Suitable enzymatic materials include the commercially available lipases, cutinases, amylases, neutral and alkaline proteases, esterases, cellulases, pectinases, lactases and peroxidases conventionally incorporated into detergent compositions. Suitable enzymes are discussed in U.S. Pat. Nos. 3,519,570 and 3,533,139.

Peroxidases are haemoproteins specific for peroxide, but using a wide range of substances as donors. Catalase which decomposes peroxide, is included here in view of the fact that it is generally similar in structure and properties and is able to bring about certain oxidations by $H_2O_2$. The decomposition of $H_2O_2$ can be regarded as the oxidation of one molecule by the other. It is widespread in aerobic cells and may have some more important function. The coenzyme peroxidases are not haemoproteins and one at least is a flavoprotein. Other flavoproteins such as xanthine oxidase will also use $H_2O_2$ among other acceptors, and the coenzyme peroxidases resemble these rather than the classical peroxidases in not being specific for $H_2O_2$. Suitable peroxidases for the compositions of the present invention include horseradish peroxidase, Japanese radish peroxidase, cow's milk peroxidase, rat liver peroxidase, linginase and haloperoxidase such as chloro- and bromo-peroxidase.

Enzymes are optionally incorporated at levels sufficient to provide up to about 50 mg by weight, more typically about 0.01 mg to about 10 mg of active enzyme per gramm of the hair treatment composition of the invention. Stated otherwise the peroxidase enzyme may be incorporated into the compositions in accordance with the invention at a level of from about 0.0001% to about 5%, preferably from about 0.001% to about 1%, more preferably from about 0.01% to about 1% active enzyme by weight of the composition.

Commercially available protease enzymes include those sold under the trade names Alcalase, Savinase, Primase, Durazym, and Esperase by Novo Industries A/S (Denmark), those sold under the tradename Maxatase, Maxacal and Maxapem by Gist-Brocades, those sold by Genencor International, and those sold under the tradename Opticlean and Optimase by Solvay Enzymes. Protease enzyme may be incorporated into the compositions in accordance with the invention at a level of from 0.0001% to 4% active enzyme by weight of the composition.

Amylases include, for example, α-amylases obtained from a special strain of B licheniformis, described in more detail in GB-1,269,839 (Novo). Preferred commercially available amylases include for example, those sold under the tradename Rapidase by Gist-Brocades, and those sold under the tradename Termamyl and BAN by Novo Industries A/S. Amylase enzyme may be incorporated into the composition in accordance with the invention at a level of from 0.0001% to 2% active enzyme by weight of the composition.

Lipolytic enzyme may be present at levels of active lipolytic enzyme of from 0.0001% to 2% by weight, preferably 0.001% to 1% by weight, most preferably from 0.001% to 0.5% by weight of the compositions.

The lipase may be fungal or bacterial in origin being obtained, for example, from a lipase producing strain of Humicola sp., Thermomyces sp. or Pseudomonas sp. including *Pseudomonas pseudoalcaligenes* or *Pseudomas fluorescens*. Lipase from chemically or genetically modified mutants of these strains are also useful herein. A preferred lipase is derived from *Pseudomonas pseudoalcaligenes*, which is described in Granted European Patent, EP-B-0218272.

Another preferred lipase herein is obtained by cloning the gene from *Humicola lanuginosa* and expressing the gene in *Aspergillus oryza*, as host, as described in European Patent Application, EP-A-0258 068, which is commercially available from Novo Industri A/S, Bagsvaerd, Denmark, under the trade name Lipolase. This lipase is also described in U.S. Pat. No. 4,810,414, Huge-Jensen et al, issued Mar. 7, 1989.

Surfactant Materials

The compositions of the present invention can additionally contain a surfactant system. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

(i) Anionic Surfactants

Anionic surfactants suitable for inclusion in the compositions of the invention include alkyl sulphates, ethoxylated alkyl sulphates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}$–$C_{22}$, preferably $C_{12}$–$C_{18}$ more preferably $C_{12}$–$C_{14}$.

(ii) Nonionic Surfactants

The compositions of the invention can also comprise water-soluble nonionic surfactant(s). Surfactants of this class include $C_{12}$–$C_{14}$ fatty acid mono-and diethanolamides, sucrose polyester surfactants and polyhydroxy fatty acid amide surfactants having the general formula below.

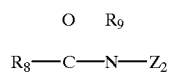

The preferred N-alkyl, N-alkoxy or N-aryloxy, polyhydroxy fatty acid amide surfactants according to the above formula are those in which $R_8$ is $C_5$–$C_{31}$ hydrocarbyl, preferably $C_6$–$C_{19}$ hydrocarbyl, including straight-chain and branched chain alkyl and alkenyl, or mixtures thereof and $R_9$ is typically hydrogen, $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH)$—$CH_2OH$, where n is an integer from 1 to 5, inclusive, and R' is H or a cyclic mono- or polysaccharide, and alkoxylated derivatives thereof. As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a C6–C19 straight chain alkyl or alkenyl group. In compounds of the above formula, $R_8$—CO—N< can be, for example, cocoamide, stearamide, oleamide, lauramide, myristamide, capricamide, palmiamide, tallowamide, etc.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula below:

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl_cocoate.

Preferred for use herein are polyethyleneglycol based polyethoxylated $C_9$–$C_{15}$ fatty alcohol nonionic surfactants containing an average of from about 5 to about 50 ethyleneoxy moieties per mole of surfactant.

Suitable polyethylene glycol based polyethoxylated $C_9$–$C_{15}$ fatty alcohols suitable for use herein include $C_9$–$C_{11}$ Pareth-3, $C_9$–$C_{11}$ Pareth-4, $C_9$–$C_{11}$ Pareth-5, $C_9$–$C_{11}$ Pareth-6, $C_9$–$C_{11}$ Pareth-7, $C_9$–$C_{11}$ Pareth-8, $C_{11}$–$C_{15}$ Pareth-3, $C_{11}$–$C_{15}$ Pareth-4, $C_{11}$–$C_{15}$ Pareth-5, $C_{11}$–$C_{15}$ Pareth-6, $C_{11}$–$C_{15}$ Pareth-7, $C_{11}$–$C_{15}$ Pareth-8, $C_{11}$–$C_{15}$ Pareth-9, $C_{11}$–$C_{15}$ Parenth-10, $C_{11}$–$C_{15}$ Pareth-11, $C_{11}$–$C_{15}$ Pareth-12, $C_{11}$–$C_{15}$ Pareth-13 and $C_{11}$–$C_{15}$ Pareth-14. PEG 40 hydrogenated castor oil is commercially available under the tradename Cremophor (RTM) from BASF. PEG 7 glyceryl cocoate and PEG 20 glyceryl laurate are commercially available from Henkel under the tradenames Cetiol (RTM) HE and Lamacit (RTM) GML 20 respectively. $C_9$–$C_{11}$ Pareth-8 is commercially available from Shell Ltd under the tradename Dobanol (RTM) 91-8. Particulary preferred for use herein are polyethylene glycol ethers of ceteryl alcohol such as Ceteareth 25 which is available from BASF under the trade name Cremaphor A25.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include:

(a) imidazolinium surfactants of formula (VII)

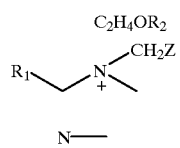

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (VIII)

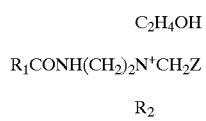

wherein $R_1$, $R_2$ and Z are as defined above;

(b) aminoalkanoates of formula (IX)

$$R_1NH(CH_2)_nCO_2M$$

iminodialkanoates of formula (X)

$$R_1N[(CH_2)_mCO_2M]_2$$

and iminopolyalkanoates of formula (XI)

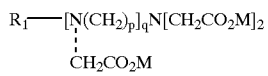

wherein n, m, p, and q are numbers from 1 to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula (VII), although the CTFA Cosmetic Ingredient Dictionary, 3rd Edition indicates the non-cyclic structure (VIII) while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula XII and/or XIII in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals). Further examples of amphoteric surfactants suitable for use herein include Octoxynol-1 (RTM), polyoxethylene (1) octylphenyl ether; Nonoxynol-4 (RTM), polyoxyethylene (4) nonylphenyl ether and Nonoxynol-9, polyoxyethylene (9) nonylphenyl ether.

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

(iv) Zwitterionic Surfactants

Water-soluble auxiliary zwitterionic surfactants suitable for inclusion in the compositions of the present invention include alkyl betaines of the formula $R_5R_6R_7N^+(CH_2)_nCO_2M$ and amido betaines of the formula (XII) below:

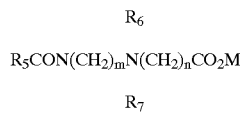

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine (RTM).

Water-soluble auxiliary sultaine surfactants suitable for inclusion in the compositions of the present invention include alkyl sultaines of the formula (XIII) below:

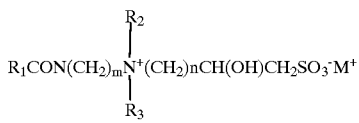

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble auxiliary amine oxide surfactants suitable for inclusion in the compositions of the present invention include alkyl amine oxide $R_5R_6R_7NO$ and amido amine oxides of the formula (XIV) below:

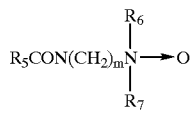

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

Optional Materials

A number of additional optional materials can be added to the coloring compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercaptans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and ρ-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4$ Cl); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; hair conditioning agents such as silicones, higher alcohols, cationic polymers and the like; enzyme stabilisers such as water soluble sources of calcium or borate species; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. and water softening agents such as sodium citrate.

The present invention is represented by the following non-limiting examples. In the examples, all concentrations are on a 100% active basis and all percentages are by weight unless otherwise stated and the abbreviations have the following designations:

| | |
|---|---|
| Oxidising agent 1 | hydrogen peroxide |
| Oxidising agent 2 | peracetic acid |
| Oxidative Dye 1 | para-phenylene diamine |
| Oxidative Dye 2 | para-aminophenol |
| Oxidative Dye 3 | meta-aminophenol |
| Oxidative Dye 4 | 2-amino-3-hydroxy pyridine |
| Oxidative Dye 5 | 4-amino-2-hydroxy toluene |
| Non-oxidative Dye | Basic red 76 |
| Chelating agent | Ethylenediamine tetraaceticacid |
| Surfactant 1 | Ceteareth-25 |
| Surfactant 2 | Cocoamidopropyl betaine |
| Thickener 1 | Cetyl alcohol |
| Thickener 2 | Stearyl alcohol |
| Antioxidant | Sodium sulphite |
| Buffering Agent | Acetic acid |

EXAMPLES I–VII

The following are hair treatment compositions in the form of hair coloring compositions which are representative of the present invention.

| Ingredient | I | II | III | IV | V | VI | VII |
|---|---|---|---|---|---|---|---|
| Oxidising Agent 1 | 0.7 | 0.7 | 0.7 | 0.7 | 0.7 | — | 0.2 |
| Oxidising Agent 2 | — | — | — | — | — | 2.0 | 0.5 |
| Oxidative Dye 1 | 0.24 | 0.14 | 0.24 | 0.15 | 0.24 | 0.475 | 0.24 |
| Oxidative Dye 2 | 0.09 | 0.05 | 0.009 | 0.5 | 0.09 | 0.18 | — |
| Oxidative Dye 3 | 0.006 | 0.004 | 0.006 | — | 0.006 | 0.012 | 0.006 |
| Oxidative Dye 4 | 0.06 | 0.03 | 0.06 | 0.1 | 0.06 | 0.11 | 0.06 |

-continued

| Ingredient | I | II | III | IV | V | VI | VII |
|---|---|---|---|---|---|---|---|
| Oxidative Dye 5 | — | — | — | 0.5 | — | — | — |
| Non-Oxidative Dye | — | — | — | — | — | — | 0.1 |
| Surfactant 1 | 1.5 | 1.7 | 1.5 | 1.5 | 1.5 | 3.0 | — |
| Surfactant 2 | — | — | — | — | — | — | 1.5 |
| Chelating agent | 0.1 | 0.06 | 0.09 | 0.2 | 0.1 | 0.2 | 0.1 |
| Thickener 1 | 2.3 | 2.6 | 2.3 | 2.3 | 2.3 | 4.5 | 2.3 |
| Thickener 2 | 2.3 | 2.6 | 2.3 | 2.3 | 2.3 | 4.5 | 2.3 |
| Antioxidant | 0.1 | 0.06 | 0.1 | 0.2 | 0.1 | 0.2 | 0.1 |
| Buffer | — | — | — | 0.5 | 0.5 | — | — |
| Water | ... to balance ... | | | | | | |
| pH | 4.0 | 3.8 | 3.9 | 4.6 | 2.7 | 2.4 | — |

In the examples, water is used as the diluent. However in variations hereof water can be replaced, in part, by from about 0.5% to about 50% by weight of the total water content of the examples by diluents such as lower alcohols, e.g., ethylene glycol, ethylene glycol monoethyl ether, diethylene glycol, diethylene glycol monoethyl ether, propylene glycol, 1,3-propane diol, ethanol, isopropyl alcohol, glycerine, butoxyethanol, ethoxydiglycol, hexylene glycol, polyglyceryl-2-oleyl ether and mixtures thereof.

Experimental Methods

I. Assessment of Initial Color and Color Change

The equipment used to measure both the initial color and color change on substrates (hair/skin) dyed with the singly packaged low pH coloring compositions of the present invention is a Hunter Colorquest spectrophotometer. The value used to express the degree of color change on any particular substrate is Delta E ($\Delta E$). Delta E, as defined herein, is represented by a factual sum of L, a, and b values such that:

$$\Delta E = (\Delta L^2 + \Delta a^2 + \Delta b^2)^{1/2}$$

and L is a measure of lightness and darkness (color intensity), wherein L=100 is equivalent to white, and L=0 is equivalent to black. Further, 'a' is a measure of the red and green quotients (color hues) such that positive equates to red and negative equates to green, and 'b'. is a measure of the yellow and blue quotients (color hues) such that positive equates to yellow and negative equates to blue.

Hunter Colorquest measurements can be carried out on the Hunter Labscan Colorimeter which is full scanning spectrocolorimeter with a wavelength of from 400–700 nanometers which records the color of test hair switches (tresses) in terms of 'L', 'a' and 'b' values. The machine is set to: mode—0/45; port size—1 inch; view size—1 inch; light—D65; field of view—10°; UV lamp/filter—none. The hair is placed in a sample holder designed to hold the hair in a uniform orientation during measurement. Equivalent colorimeters can be used, but it must be ensured that the hair does not move during measurement. The hair must be spread to cover the 1 inch port during color measurement. Dots are placed on the switch holder to guide the positioning of the holder at the port. The dots are lined up with a mark on the port and readings are taken at each spot.

Eight measurements are run per switch, 4 on each side, and three switches are run per treatment.

II. Assessment of Color Retention Potential

The equipment used to measure both the initial color potential (Delta E Target) and color development potential after a period of storage (Delta E stored) for any given singly packaged hair coloring composition is, as hereinbefore detailed, a Hunter Colorquest Spectrophotometer.

Target Delta E, $\Delta E_T$, represents the color developed by the composition on its first (initial) application to the hair. Stored Delta E, $\Delta E_S$, represents the color developed by that composition after a period of storage (at about room temperature, 25° C.). The start of the period of storage, X, is defined herein as time zero, i.e. from the point of initial use of the composition to color hair at low pH. The storage period can be from a few days up to several months.

The color retention potential, $\Delta E_P$, can be expressed as the difference between the initial color development $\Delta E_T$ and the color development after storage $\Delta E_S$ as illustrated by the following formula:

$$\Delta E_P = \Delta E_T - \Delta E_S$$

The smaller the difference between $\Delta E_T$ and $\Delta E_S$ the higher the color development potential $\Delta E_P$.

In preferred compositions according to the present invention $\Delta E_P$ after at least about 1 hour (60 minutes) of storage is less than about 2, preferably less than about 1, more preferably less than about 0.2. After at least about 1 day (24 hours) $\Delta E_P$ is less than about 2, preferably less than about 1, more preferably less than about 0.3. After at least about 1 month $\Delta E_P$ is less than about 3, preferably less than about 1.5, more preferably less than about 0.3.

The relative change in color development potential after a period of storage (X), % $\Delta E_P$, can also be expressed in terms of the percentage of initial target color $\Delta E_T$, which is delivered to the hair after storage. As such, the percentage of color development potential for any given composition can be expressed by the following formula:

$$\% \Delta E_P = \Delta E_T - \Delta E_S / \Delta E_T \times 100$$

In preferred compositions according to the present invention the color delivered to the hair at least 1 hour (60 minutes) of storage (Delta E stored) at room temperature (25° C.) is greater than about 75%, preferably greater than about 80%, more preferably greater than about 85%, most preferably greater than about 90% and especially greater than about 95% of the color delivered to the hair on first application (Delta E initial).

In preferred compositions according to the present invention the color delivered to the hair after at least 1 day (24 hours) of storage (Delta E stored) at room temperature (25° C.) is greater than about 75%, preferably greater than about 80%, more preferably greater than about 85%, most preferably greater than about 90% and especially greater than about 95% of the color delivered to the hair on first application (Delta E initial).

In preferred compositions according to the present invention the color delivered to the hair after at least 1 month of storage (Delta E stored) at room temperature (25° C.) is greater than about 75%, preferably greater than about 80%, more preferably greater than about 85%, most preferably greater than about 90% and especially greater than about 95% of the color delivered to the hair on first application (Delta E initial).

III. Standard Hair Switch

The compositions according to the present invention can be used to color hair of all colors, types and condition. For the purposes of illustration two test hair switch types; light brown and light brown with 40% grey coverage have been tested herein. These standard hair switches can be measured in terms of their approximate L, a, b values.

|  | L | a | b |
|---|---|---|---|
| Light brown | 60 | 9 | 32 |
| 40% grey light brown | 35–37 | 4.5–5.5 | 11.5–12.7 |

IV Hair Switch Coloring Method

To color hair, a 4 gramme switch of about 8 inch long hair is hung over a suitable container. The test coloring product is then prepared (i.e., where applicable the separate bottle components are mixed together) and about 8 grammes of product is applied directly to the test hair switch. The colorant is massaged through the hair switch for up to about 1 minute and then left on the hair switch for up to about 30 minutes. After rinsing with running water for about 1 or 2 minutes the colored hair switch is then cleansed (according to the shampoo protocol) and dried. Drying can be effected either naturally (without heat assistance) or using a drier. The color development (initial color) of the colored, cleansed, dried test hair switch can then be assessed using the Hunter Colorquest spectrophotometer.

For the delivery of a red shade (hue) to prepermed, prebleached light brown hair (having L, a, b values of approximately 60, 9 and 32) the preferred initial shade of the colored hair will have a hue value (arc tangent of (b/a)) in the range of from about 25 to about 70, more preferably from about 30 to about 65, most preferably from about 35 to about 60 and wherein the initial color intensity (L) is greater than about 10 and less than about 70, preferably greater than about 15 and less than about 65, more preferably greater than about 20 and less than about 60.

For the delivery of a brown or black shade (hue) to prepermed, prebleached light brown hair (having L, a, b values of approximately 60, 9 and 32) the preferred initial shade of the colored hair will have a hue value (arc tangent of (b/a)) of less than about 25, preferably less than about 20 and the initial color intensity (L) will be greater than about 1 and less than about 50, preferably greater than about 5 and less than about 45.

For the delivery of a light brown shade (hue) to prepermed, prebleached light brown hair (having L, a, b values of approximately 60, 9 and 32) the preferred initial shade of the colored hair will have a hue hue value (arc tangent of (b/a)) in the range of from about 70 up to about 110 and wherein the initial color intensity (L) will be greater than about 20 and less than about 95, preferably greater than about 25 and less than about 90.

V. Hair Switch Cleansing Method

Switches of colored hair are subjected to a repeated cleansing cycle wherein the following process is repeated up to 10 times.

A 4 gramme, 8 inch test switch of colored hair is clamped over a suitable container and rinsed thoroughly for about 10 seconds using warm water (at about 100° F. at about 1.5 gallons/minute pressure). Shampoo (about 0.4 ml non-conditioning shampoo) can then be applied directly to the wet test switch using a syringe. After lathering the hair for about 30 seconds the hair is rinsed in running warm water for about 30 seconds. The shampoo and lathering process is then repeated with a final 60 second rinse. Excess water can be removed (squeezed) from the test switch using the fingers. The test switch is then dried either natrually, or using a pre-heated dryer box at about 140° F. (for about 30 minutes). The colored, cleansed, dried test hair switch can then be color assessed (Delta E fade).

During any single test cycle each different switch to be assessed should be tested in water of equivalent temperature, pressure level and hardness level.

Delta E fade results for prepermed, prebleached light brown hair (having L, a, b values of approximately 60, 9 and 32) which has been colored a red shade (of hue value in the range of from about 25 to about 70) are generally less than about 5.0, preferably less than about 4.5, more preferably less than about 4.0 and wherein the change in hair color, % delta E, after up to 20 washes, is less than about 20%, and preferably less than about 15%, more preferably less than about 10%.

Delta E fade results for prepermed, prebleached light brown hair (having L, a, b values of approximately 60, 9 and 32) which has been colored a brown or black shade (of hue value of less than about 25) are generally less than about 2.3, preferably less than about 2.0, more preferably less than about 1.7 and wherein the change in hair color, % delta E, after up to 20 washes, is less than about 5%, preferably less than about 4.5%, more preferably less than about 4%, most preferably less than about 3.5%.

Delta E fade results for prepermed, prebleached light brown hair (having L, a, b values of approximately 60, 9 and 32) which has been colored a light brown shade (of hue value in the range of from about 70 to about 110) are generally less than about 2.6, preferably less than about 2.3 and wherein the change in hair color, % delta E, after up to 20 washes, is less than about 15%, preferably less than about 12%, more preferably less than about 10%, most preferably less than about 8%.

VI. Skin Staining Test Method

For the purposes of the invention skin staining results are based on pig skin data.

Skin staining measurements can be made on pigs ears, preferably the ears of recently deceased pigs. The ears should not have been subject to undue heating (scalding). Hair is shaved from the most flat section of the ear to be stained. An area of at least 1 cm×5 cm is pre-marked on the ear (using a permenant marker) and the ear is then cleansed with non-conditioning shampoo (0.1 $g/cm^2$ at 10% dilution). After massaging in the shampoo for about 1 minute the ear is rinsed for about 30 seconds then gently patted dry by hand with a paper towel. Baseline color assessment readings (L, a, b) are then taken for the pre-marked area. The test dye is then applied to the pre-marked test area (about 0.25 $g/cm^2$) and massaged in for about 1 minute and allowed to remain on the ear for about 30 minutes. The colored ear is then rinsed with about 2 litres of tap water at about 37° C. and hand dried as above. Color assessment readings (L, a, b) are then taken for the pre-marked area of the dyed ear. Total color change (Delta E) can then be calculted from the L, a, b values and expressed as relative levels of skin staining (versus the baseline color).

VII. Measurement of pH

For the purposes of the present invention, as described herein, all pH measurements were carried out on a Mettler Toledo 320 pH meter. All pH measurements of dyes, oxidising agents and mixtures thereof, either singly or in combination with a suitable delivery medium, such as water and surfactant and/or thickeners, were carried out at room temperature (about 25° C.). The pH of dye mixtures were measured in the form of intended use and prior to application. A preferred delivery medium for use herein comprises an emulsion of ceteareth-25 at a level of from about 1% to about 3% by weight, cetyl alohol at a level of from about 2% to about 5% by weight and stearyl alcohol at a level of from about 2% to about 5% of solution or composition.

Experimental Data

I. Color Retention Potential (Color Delivered after Storage)

Example formulae I–VII provide improved color retention potential over time versus similar compositions having pH outside the scope of the present invention.

II. Initial Color and Wash Fastness

Example formula I provides improved initial color and fade resistance versus a similar composition having pH outside the scope of the present invention.

Example formula II provides improved intial color development and washfastness versus a similar high pH formula containing the same level of oxidant and up to 60% more dye.

Example formula III provides improved initial color development versus a high pH formula containing the same level of dye but more inorganic peroxygen oxidising agent.

III. Relative Skin Staining

Example formula IV provides reduced levels of skin staining on a pigs ear versus an equivalent composition at high pH.

Method of Manufacture

It is important that dyeing compositions be in a form which is easy and convenient to prepare and use by the consumer, since the oxidising agent must remain in contact with the hair for a certain period of time and not run or drip off of the hair, possibly causing eye or skin irritation.

To address the above, the coloring compositions of the present invention are provided in the form of a single pack comprising oxidising and colorisng components. The coloring compositions of the present invention can either be used to color hair after purchase, or partially used to color hair and the remainder stored for future use, or wholly stored for future use.

As hereinbefore described the compositions according to the present invention are provided to the consumer as a single component package. Such a single pack would comprise a single solution at pH 1 to about 5 containing both the oxidising agent and the oxidative dye precursors and additional, optional, agents such as surfactants, antioxidants, thickeners etc. The solution would be applied directly to the hair by the consumer without the need for any pretreatments or mixing, thereby providing a simple, fast, easy to use, 'no-mess' hair coloring system. A further advantage of such a single component system is that it could be stored and re-used i.e., a single package could contain enough coloring composition for several applications over time.

Thus, according to a further aspect of the present invention, there is provided:

A method for coloring hair wherein a hair coloring mixture is present in a single package and applied directly to the hair and wherein the hair coloring mixture comprises:

(a) from about 0.01% to about 6% by weight of an oxidising agent; and (b) from about 0.001% to about 5% by weight of an oxidative hair coloring agent wherein the combined mixture of (a) and (b) has a pH in the range of from about 1 to about 6 and wherein the resultant color delivered to the hair (Delta E), after at least about 1 month of storage at room temperature, is greater than about 75%, preferably greater than about 85%, more preferably greater than about 90% and most preferably greater than about 95% of the total color delivered to the hair (Delta E) from a mixture of (a) and (b) on application.

Method of Use

The singly packaged compositions herein described are used to color hair. The coloring compositions herein are applied to the hair for periods of from 1 minute to 60 minutes depending upon the degree of coloring required. A preferred time is between 5 minutes and 30 minutes. The coloring compositions according to the present invention can be applied to hair both wet and dry hair.

As hereinbefore described the coloring composition are present as a single package, containing both oxidising agent and oxidative hair coloring agent in a storage stable mixture, at low pH, suitable for direct application to the hair. Hair coloring compositions according to the present invention can be used to color the hair in several ways including:

(i) the pre-mixed, low pH, single kit component is applied directly to the hair.

(ii) the pre-mixed, low pH, single kit component is applied directly to the hair after a period of storage at room temperature.

The products according to the present invention are storage stable and re-usuable usable and provide excellent initial hair coloring and in-use efficacy benefits.

What is claimed is:

1. A hair coloring composition suitable for direct application to hair and comprising a singly packaged mixture of:

(a) an inorganic peroxygen oxidising agent; and (b) an oxidative hair coloring agent comprising an aromatic diamine, polyhydric phenol or amino phenol;

wherein the mixture of (a) and (b) has a pH in the range of from about 1 to about 5 and wherein the hair coloring composition is adapted to provide, after storage of the composition for one month, a change in hair color, Delta E Stored, upon application of the composition to the hair, wherein Delta E Stored is at least about 75% of a Delta E Target, wherein Delta E Target is a change in hair color provided by application of a mixture of (a) and (b) immediately after mixing (a) and (b), wherein each Delta E is determined by a Hunter Colorquest spectrophotometer and Delta $E=(\Delta_L^2+\Delta_a^2+\Delta_b^2)/2$, and wherein L is a measurement of the color intensity, a is a measure of the red and green quotients, and b is a measure of the yellow and blue quotients.

2. A composition accoring to claim 1 wherein the oxidative hair coloring agent is present at a level of from abot 0.01% to about 4% by weight.

3. A composition according to claim 1 wherein the aromatic diamine, polyhydric phenol or amino phenol is a primary intermediate, and wherein the oxidative hair coloring agent further comprises a secondary intermediate.

4. A composition according to claim 3 wherein the primary intermediate comprises pyrogallol, resorcinol, p-toluenediamine, p-phenylenediamine, o-phenylenediamine, m-phenylenediamine, o-aminophenol, p-aminophenol, 4-aminonitrophenol, nitro-p-phenylenediamine, N-phenyl-p-phenylenediamine, m-aminophenol, 2-amino-3-hydroxypyridine, 1-napthol, N,N-bis-(2-hydroxyethyl) p-phenylenediamine, 4-amino-2-hydroxytoluene, 1,5-dihydroxynapthalene, 2-methyl resorcinol, or 2,4-diaminoanisole.

5. A composition according to claim 1 wherein the aromatic diamine comprises a compound of the general formula:

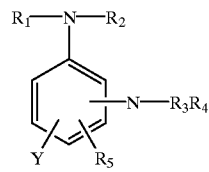

wherein Y is hydrogen, halogen, nitro, amino, hydroxyl, —C(O)H, —COOM or —SO$_3$M where M is hydrogen, alkali or alkaline earth metal ion, ammonium, or substituted ammonium wherein one or more hydrogens of the ammonium ion are replaced with a $C_1$ to $C_3$ alkyl or hydroxyalkyl radical, wherein $R_1$, $R_2$, $R_3$ and $R_4$ are independently selected from the group consisting of hydrogen, $C_1$ to $C_4$ alkyl and alkenyl, and $C_6$ to $C_9$ aryl, alkaryl and aralkyl, and wherein $R_5$ is hydrogen, $C_1$ to $C_4$ unsubstituted or substituted alkyl or alkenyl, or $C_6$ to $C_9$ unsubstituted or substituted aryl, alkaryl or aralkyl, wherein the substituents are selected from hydrogen, halogen, nitro, amino, hydroxyl, —C(O)H, —COOM and $SO_3M$, or a peroxide-compatible salt thereof.

6. A composition according to claim 1 wherein the amino phenol comprises a compound of the general formula:

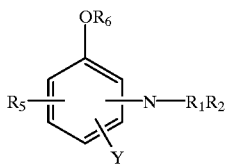

wherein Y is hydrogen, halogen, nitro, amino, hydroxyl, —C(O)H, —COOM or —$SO_3M$ where M is hydrogen, an alkali or alkaline earth metal, ammonium, or substituted ammonium wherein one or more hydrogens of the ammonium ion are replaced with a $C_1$ to $C_3$ alkyl or hydroxyalkyl radical, wherein $R_1$ and $R_2$ are independently selected from the group consisting of hydrogen, $C_1$ to $C_4$ alkyl or alkenyl and $C_6$ to $C_9$ aryl, alkaryl or aralkyl, $R_5$ is hydrogen, $C_1$ to $C_4$ unsubstituted or substituted alkyl or alkenyl, or $C_6$ to $C_9$ unsubstituted or substituted aryl, alkaryl or aralkyl, and $R_6$ is hydrogen or $C_1$ to $C_4$ substituted or unsubstituted alkyl or alkenyl, wherein the substituents are selected from hydrogen, halogen, nitro, amino, hydroxyl, —C(O)H, —COOM and $SO_3M$, or a peroxide-compatible salt thereof.

7. A composition according to claim 1 wherein the polyhydric phenol comprises a compound of the general formula:

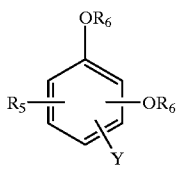

wherein Y is hydrogen, halogen, nitro, amino, hydroxyl, —C(O)H, —COOM or —$SO_3M$ where M is hydrogen, an alkali or alkaline earth metal, ammonium, or substituted ammonium wherein one or more hydrogens of the ammonium ion are replaced with a $C_1$ to $C_3$ alkyl or hydroxyalkyl radical, wherein $R_5$ is hydrogen, $C_1$ to $C_4$ unsubstituted or substituted alkyl or alkenyl, or $C_6$ to $C_9$ unsubstituted or substituted aryl, alkaryl or aralkyl, and wherein $R_6$ is hydrogen or $C_1$ to $C_4$ substituted or unsubstituted alkyl or alkenyl, wherein the substituents are selected from hydrogen, halogen, nitro, amino, hydroxyl, —C(O)H, —COOM and $SO_3M$, or a peroxide-compatible salt thereof.

8. A composition according to claim 1 wherein the Delta E Stored is at least 85% of the Delta E Target.

9. A composition according to claim 1, wherein the Delta E Stored is at least 90% of the Delta E Target.

10. A composition according to claim 1, wherein the pH of the composition is in the range of from about 1.5 to about 5.

11. A composition according to claim 1 wherein the pH of the composition is in the range of from 1.8 to about 4.7.

12. A composition according to claim 1 wherein the pH of the composition is in the range of from about 2.5 to about 4.

13. A composition according to claim 1 wherein the composition further comprises preformed organic peroxyacid oxidising agent, organic peroxide oxidising agent or mixtures thereof.

14. A composition according to claim 1 wherein the inorganic peroxygen oxidising agent is present at a level of from about 0.01% to about 2% by weight of the composition.

15. A composition according to claim 1 wherein the inorganic peroxygen oxidising agent is hydrogen peroxide.

16. A composition according to claim 1, wherein the oxidative hair coloring agent is present at a level of from about 0.1% to about 1% by weight.

17. A composition according to claim 1 wherein the oxidative hair coloring agent is present at a level of from about 0.001% to about 3% by weight.

18. A composition according to claim 1 additionally comprising one or more buffering agents.

19. A composition according to claim 18 wherein the buffering agent comprises an organic or inorganic acid having a first pKa below pH 6.

20. A composition according to claim 1 additionally comprising one or more surfactants selected from anionic, nonionic, cationic, zwitterionic, and amphoteric surfactants and mixtures thereof.

21. A composition according to claim 1 additionally comprising one or more cosmetically acceptable materials comprising thickening agents, stabilisers, or antioxidants.

* * * * *